(12) United States Patent
Liran et al.

(10) Patent No.: US 9,331,791 B2
(45) Date of Patent: May 3, 2016

(54) TRANSFER OF POWER AND DATA

(71) Applicant: Nano Retina Ltd., Herzliya Pituach (IL)

(72) Inventors: Tuvia Liran, Qiryat Tivon (IL); Ra'anan Gefen, Re'ut (IL); Leonid Yanovitz, Rishon Lezion (IL)

(73) Assignee: NANO RETINA LTD., Herzliya Pituach (IL)

( * ) Notice: Subject to any disclaimer, the term of this patent is extended or adjusted under 35 U.S.C. 154(b) by 91 days.

(21) Appl. No.: 14/160,314

(22) Filed: Jan. 21, 2014

(65) Prior Publication Data
US 2015/0207572 A1    Jul. 23, 2015

(51) Int. Cl.
| | | |
|---|---|---|
| H04B 10/00 | (2013.01) | |
| H04B 10/80 | (2013.01) | |
| H04B 10/61 | (2013.01) | |
| G08C 23/04 | (2006.01) | |
| A61N 1/372 | (2006.01) | |
| A61N 1/378 | (2006.01) | |
| H01L 31/00 | (2006.01) | |
| A61N 1/36 | (2006.01) | |

(52) U.S. Cl.
CPC ............ *H04B 10/807* (2013.01); *A61N 1/3727* (2013.01); *A61N 1/3787* (2013.01); *G08C 23/04* (2013.01); *H01L 31/00* (2013.01); *H04B 10/6164* (2013.01); *A61N 1/36046* (2013.01)

(58) Field of Classification Search
CPC ..................... H04B 10/807; H04B 10/6164
See application file for complete search history.

(56) References Cited

U.S. PATENT DOCUMENTS

| | | | |
|---|---|---|---|
| 1,662,446 A | 3/1928 | Wappler |
| 2,721,316 A | 10/1955 | Shaw |
| 2,760,483 A | 8/1956 | Tassicker |
| 4,262,294 A | 4/1981 | Hara et al. |
| 4,272,910 A | 6/1981 | Danz |
| 4,551,149 A | 11/1985 | Sciarra |
| 4,601,545 A | 7/1986 | Kern |
| 4,628,933 A | 12/1986 | Michelson |
| 4,664,117 A | 5/1987 | Beck |

(Continued)

FOREIGN PATENT DOCUMENTS

| | | |
|---|---|---|
| CA | 2235216 | 4/1997 |
| CN | 1875895 | 12/2006 |

(Continued)

OTHER PUBLICATIONS

Forzati, Marco, Anders Berntson, and Jonas Mårtensson. "Phase Modulation Techniques for Suppression of IFWM in OOK Transmission."

(Continued)

*Primary Examiner* — Dzung Tran
(74) *Attorney, Agent, or Firm* — Sughrue Mion, PLLC

(57) ABSTRACT

Apparatus and methods are described, including a method for transmission of power and data during a plurality of consecutive time intervals. During a power-transmission portion of each of the plurality of consecutive time intervals, a power signal, in which no data is encoded, is transmitted. During a power-and-data-transmission portion of each of the plurality of consecutive time intervals, a power-and-data signal, in which is encoded a single bit, is transmitted. The power-and-data signal includes: (a) a high-level power-and-data signal portion, and (b) a low-level power-and-data signal portion. Other applications are also described.

16 Claims, 19 Drawing Sheets

(56) References Cited

U.S. PATENT DOCUMENTS

| | | |
|---|---|---|
| 4,786,818 A | 11/1988 | Mead et al. |
| 4,837,049 A | 6/1989 | Byers et al. |
| 4,853,943 A | 8/1989 | Laws |
| 4,903,702 A | 2/1990 | Putz |
| 4,914,738 A | 4/1990 | Oda et al. |
| 4,969,468 A | 11/1990 | Byers et al. |
| 5,016,633 A | 5/1991 | Chow |
| 5,024,223 A | 6/1991 | Chow |
| 5,081,378 A | 1/1992 | Watanade |
| 5,108,427 A | 4/1992 | Majercik et al. |
| 5,109,844 A | 5/1992 | de Juan, Jr. et al. |
| 5,133,356 A | 7/1992 | Bryan et al. |
| 5,147,284 A | 9/1992 | Fedorov et al. |
| 5,159,927 A | 11/1992 | Schmid |
| 5,215,088 A | 6/1993 | Normann et al. |
| 5,313,642 A | 5/1994 | Seigel |
| 5,314,458 A | 5/1994 | Najafi et al. |
| 5,397,350 A | 3/1995 | Chow et al. |
| 5,411,540 A | 5/1995 | Edell et al. |
| 5,476,494 A | 12/1995 | Edell et al. |
| 5,526,423 A | 6/1996 | Ohuchi et al. |
| 5,556,423 A | 9/1996 | Chow et al. |
| 5,575,813 A | 11/1996 | Edell et al. |
| 5,597,381 A | 1/1997 | Rizzo, III |
| 5,608,204 A | 3/1997 | Hofflinger et al. |
| 5,674,263 A | 10/1997 | Yamamoto et al. |
| 5,769,875 A | 6/1998 | Peckham et al. |
| 5,800,478 A | 9/1998 | Chen et al. |
| 5,800,533 A | 9/1998 | Eggleston et al. |
| 5,800,535 A | 9/1998 | Howard, III |
| 5,835,250 A | 11/1998 | Kanesaka |
| 5,836,996 A | 11/1998 | Doorish |
| 5,837,995 A | 11/1998 | Chow et al. |
| 5,850,514 A | 12/1998 | Gonda et al. |
| 5,865,839 A | 2/1999 | Doorish |
| 5,873,901 A | 2/1999 | Wu et al. |
| 5,895,415 A | 4/1999 | Chow et al. |
| 5,935,155 A | 8/1999 | Humayun et al. |
| 5,944,747 A | 8/1999 | Greenberg et al. |
| 5,949,064 A | 9/1999 | Chow et al. |
| 6,020,593 A | 2/2000 | Chow et al. |
| 6,032,062 A | 2/2000 | Nisch |
| 6,035,236 A | 3/2000 | Jarding et al. |
| 6,043,437 A | 3/2000 | Schulman et al. |
| 6,069,365 A | 5/2000 | Chow et al. |
| 6,075,251 A | 6/2000 | Chow et al. |
| 6,201,234 B1 | 3/2001 | Chow et al. |
| 6,230,057 B1 | 5/2001 | Chow et al. |
| 6,259,937 B1 | 7/2001 | Schulman et al. |
| 6,287,372 B1 | 9/2001 | Briand et al. |
| 6,298,270 B1 | 10/2001 | Nisch et al. |
| 6,324,429 B1 | 11/2001 | Shire et al. |
| 6,347,250 B1 | 2/2002 | Nisch et al. |
| 6,368,349 B1 | 4/2002 | Wyatt et al. |
| 6,389,317 B1 | 5/2002 | Chow et al. |
| 6,400,989 B1 | 6/2002 | Eckmiller |
| 6,427,087 B1 | 7/2002 | Chow et al. |
| 6,442,431 B1 | 8/2002 | Veraart et al. |
| 6,458,157 B1 | 10/2002 | Suaning |
| 6,472,122 B1 | 10/2002 | Schulman et al. |
| 6,473,365 B2 | 10/2002 | Joh et al. |
| 6,498,043 B1 | 12/2002 | Schulman et al. |
| 6,507,758 B1 | 1/2003 | Greenberg et al. |
| 6,533,798 B2 | 3/2003 | Greenberg et al. |
| 6,574,022 B2 | 6/2003 | Chow et al. |
| 6,611,716 B2 | 8/2003 | Chow et al. |
| 6,647,297 B2 | 11/2003 | Scribner |
| 6,658,299 B1 | 12/2003 | Dobelle |
| 6,677,225 B1 | 1/2004 | Ellis et al. |
| 6,678,458 B2 | 1/2004 | Ellis et al. |
| 6,683,645 B1 | 1/2004 | Collins et al. |
| 6,738,672 B2 | 5/2004 | Schulman et al. |
| 6,755,530 B1 | 6/2004 | Loftus et al. |
| 6,758,823 B2 | 7/2004 | Pasquale et al. |
| 6,761,724 B1 | 7/2004 | Zrenner et al. |
| 6,762,116 B1 | 7/2004 | Skidmore |
| 6,770,521 B2 | 8/2004 | Visokay et al. |
| 6,785,303 B1 | 8/2004 | Holzwarth et al. |
| 6,792,314 B2 | 9/2004 | Byers et al. |
| 6,804,560 B2 | 10/2004 | Nisch et al. |
| 6,821,154 B1 | 11/2004 | Canfield et al. |
| 6,844,023 B2 | 1/2005 | Schulman et al. |
| 6,847,847 B2 | 1/2005 | Nisch et al. |
| 6,888,571 B1 | 5/2005 | Koshizuka et al. |
| 6,904,239 B2 | 6/2005 | Chow et al. |
| 6,908,470 B2 | 6/2005 | Stieqlitz et al. |
| 6,923,669 B1 | 8/2005 | Tsui et al. |
| 6,935,897 B2 | 8/2005 | Canfield et al. |
| 6,949,763 B2 | 9/2005 | Ovadia et al. |
| 6,961,619 B2 | 11/2005 | Casey |
| 6,970,745 B2 | 11/2005 | Scribner |
| 6,974,533 B2 | 12/2005 | Zhou |
| 6,976,998 B2 | 12/2005 | Rizzo et al. |
| 6,990,377 B2 | 1/2006 | Gliner et al. |
| 6,999,685 B1 | 2/2006 | Kawase et al. |
| 7,001,608 B2 | 2/2006 | Fishman et al. |
| 7,003,354 B2 | 2/2006 | Chow et al. |
| 7,006,873 B2 | 2/2006 | Chow et al. |
| 7,025,619 B2 | 4/2006 | Tsui et al. |
| 7,027,874 B1 | 4/2006 | Sawan et al. |
| 7,031,776 B2 | 4/2006 | Chow et al. |
| 7,035,692 B1 | 4/2006 | Maghribi et al. |
| 7,037,943 B2 | 5/2006 | Peyman |
| 7,047,080 B2 | 5/2006 | Palanker et al. |
| 7,058,455 B2 | 6/2006 | Huie, Jr. et al. |
| 7,071,546 B2 | 7/2006 | Fey et al. |
| 7,079,881 B2 | 7/2006 | Schulman et al. |
| 7,081,630 B2 | 7/2006 | Saini et al. |
| 7,096,568 B1 | 8/2006 | Nilsen et al. |
| 7,103,416 B2 | 9/2006 | Ok et al. |
| 7,107,097 B2 | 9/2006 | Stern et al. |
| 7,127,286 B2 | 10/2006 | Mech et al. |
| 7,127,301 B1 | 10/2006 | Okandan et al. |
| 7,130,693 B1 | 10/2006 | Montalbo |
| 7,133,724 B2 | 11/2006 | Greenberg et al. |
| 7,139,612 B2 | 11/2006 | Chow et al. |
| 7,147,865 B2 | 12/2006 | Fishman et al. |
| 7,149,586 B2 | 12/2006 | Greenberg et al. |
| 7,158,834 B2 | 1/2007 | Paul, Jr. |
| 7,158,836 B2 | 1/2007 | Suzuki |
| 7,160,672 B2 | 1/2007 | Schulman et al. |
| 7,162,308 B2 | 1/2007 | O'Brien et al. |
| 7,177,697 B2 | 2/2007 | Eckmiller et al. |
| 7,190,051 B2 | 3/2007 | Mech et al. |
| 7,191,010 B2 | 3/2007 | Ohta et al. |
| 7,224,300 B2 | 5/2007 | Dai et al. |
| 7,224,301 B2 | 5/2007 | Dai et al. |
| 7,235,350 B2 | 6/2007 | Schulman et al. |
| 7,242,597 B2 | 7/2007 | Shodo |
| 7,244,027 B2 | 7/2007 | Sumiya |
| 7,248,928 B2 | 7/2007 | Yagi |
| 7,251,528 B2 | 7/2007 | Harold |
| 7,255,871 B2 | 8/2007 | Huie, Jr. et al. |
| 7,257,446 B2 | 8/2007 | Greenberg et al. |
| 7,263,403 B2 | 8/2007 | Greenberg et al. |
| 7,271,525 B2 | 9/2007 | Byers et al. |
| 7,272,447 B2 | 9/2007 | Stett et al. |
| 7,291,540 B2 | 11/2007 | Mech et al. |
| 7,295,872 B2 | 11/2007 | Kelly et al. |
| 7,302,598 B2 | 11/2007 | Suzuki et al. |
| 7,305,189 B2 | 12/2007 | Martensson et al. |
| 7,314,474 B1 | 1/2008 | Greenberg et al. |
| 7,321,796 B2 | 1/2008 | Fink et al. |
| 7,342,427 B1 | 3/2008 | Fensore et al. |
| 7,377,646 B2 | 5/2008 | Suzuki |
| 7,379,000 B2 | 5/2008 | Dal et al. |
| 7,388,288 B2 | 6/2008 | Solzbacher et al. |
| 7,400,021 B2 | 7/2008 | Wu et al. |
| 7,447,547 B2 | 11/2008 | Palanker |
| 7,447,548 B2 | 11/2008 | Eckmiller |
| 7,480,988 B2 | 1/2009 | Ok et al. |
| 7,481,912 B2 | 1/2009 | Stelzle et al. |
| 7,482,957 B2 | 1/2009 | Dal et al. |
| 7,483,751 B2 | 1/2009 | Greenberg et al. |

(56) References Cited

U.S. PATENT DOCUMENTS

| | | |
|---|---|---|
| 7,493,169 B2 | 2/2009 | Greenberg et al. |
| 7,499,754 B2 | 3/2009 | Greenberg et al. |
| 7,539,544 B2 | 5/2009 | Greenberg et al. |
| 7,555,328 B2 | 6/2009 | Schulman et al. |
| 7,556,621 B2 | 7/2009 | Palanker et al. |
| 7,565,202 B2 | 7/2009 | Greenberg et al. |
| 7,565,203 B2 | 7/2009 | Greenberg et al. |
| 7,571,004 B2 | 8/2009 | Roy et al. |
| 7,571,011 B2 | 8/2009 | Zhou et al. |
| 7,574,263 B2 | 8/2009 | Greenberg et al. |
| 7,610,098 B2 | 10/2009 | McLean |
| 7,622,702 B2 | 11/2009 | Wu et al. |
| 7,630,771 B2 | 12/2009 | Cauller |
| 7,631,424 B2 | 12/2009 | Greenberg et al. |
| 7,638,032 B2 | 12/2009 | Zhou et al. |
| 7,666,523 B2 | 2/2010 | Zhou |
| 7,676,274 B2 | 3/2010 | Hung et al. |
| 7,691,252 B2 | 4/2010 | Zhou et al. |
| 7,706,887 B2 | 4/2010 | Tai et al. |
| 7,706,893 B2 | 4/2010 | Hung et al. |
| 7,709,961 B2 | 5/2010 | Greenberg et al. |
| 7,725,191 B2 | 5/2010 | Greenberg et al. |
| 7,734,352 B2 | 6/2010 | Greenberg et al. |
| 7,738,962 B2 | 6/2010 | Greenberg et al. |
| 7,749,608 B2 | 7/2010 | Laude et al. |
| 7,750,076 B2 | 7/2010 | Laude et al. |
| 7,751,896 B2 | 7/2010 | Graf et al. |
| 7,765,009 B2 | 7/2010 | Greenberg et al. |
| 7,766,903 B2 | 8/2010 | Blumenkranz et al. |
| 7,776,197 B2 | 8/2010 | Zhou |
| 7,831,309 B1 | 11/2010 | Humayun et al. |
| 7,834,767 B2 | 11/2010 | Shodo |
| 7,835,798 B2 | 11/2010 | Greenberg et al. |
| 7,840,273 B2 | 11/2010 | Schmid |
| 7,846,285 B2 | 12/2010 | Zhou et al. |
| 7,853,330 B2 | 12/2010 | Bradley et al. |
| 7,871,707 B2 | 1/2011 | Laude et al. |
| 7,877,866 B1 | 2/2011 | Greenberg et al. |
| 7,881,799 B2 | 2/2011 | Greenberg et al. |
| 7,887,681 B2 | 2/2011 | Zhou |
| 7,894,909 B2 | 2/2011 | Greenberg et al. |
| 7,894,911 B2 | 2/2011 | Greenberg et al. |
| 7,904,148 B2 | 3/2011 | Greenberg et al. |
| 7,908,011 B2 | 3/2011 | McMahon et al. |
| 7,912,556 B2 | 3/2011 | Greenberg et al. |
| 7,914,842 B1 | 3/2011 | Greenberg et al. |
| 7,937,153 B2 | 5/2011 | Zhou et al. |
| 7,957,811 B2 | 6/2011 | Caspi et al. |
| 7,962,221 B2 | 6/2011 | Greenberg et al. |
| 7,979,134 B2 | 7/2011 | Chow et al. |
| 7,989,080 B2 | 8/2011 | Greenberg et al. |
| 8,000,804 B1 | 8/2011 | Wessendorf et al. |
| 8,010,202 B2 | 8/2011 | Shah et al. |
| 8,010,206 B2 | 8/2011 | Dai et al. |
| 8,014,868 B2 | 9/2011 | Greenberg et al. |
| 8,014,869 B2 | 9/2011 | Greenberg et al. |
| 8,014,878 B2 | 9/2011 | Greenberg et al. |
| 8,024,022 B2 | 9/2011 | Schulman et al. |
| 8,034,229 B2 | 10/2011 | Zhou et al. |
| 8,046,078 B2 | 10/2011 | Greenberg et al. |
| 8,060,211 B2 | 11/2011 | Greenberg et al. |
| 8,060,216 B2 | 11/2011 | Greenberg et al. |
| 8,068,913 B2 | 11/2011 | Greenberg et al. |
| 8,078,284 B2 | 12/2011 | Greenberg et al. |
| 8,090,447 B2 | 1/2012 | Tano et al. |
| 8,090,448 B2 | 1/2012 | Greenberg et al. |
| 8,103,352 B2 | 1/2012 | Fried et al. |
| 8,121,697 B2 | 2/2012 | Greenberg et al. |
| 8,131,375 B2 | 3/2012 | Greenberg et al. |
| 8,131,378 B2 | 3/2012 | Greenberg et al. |
| 8,145,322 B1 | 3/2012 | Yao et al. |
| 8,150,526 B2 | 4/2012 | Gross et al. |
| 8,150,534 B2 | 4/2012 | Greenberg et al. |
| 8,160,713 B2 | 4/2012 | Greenberg et al. |
| 8,165,680 B2 | 4/2012 | Greenberg et al. |
| 8,170,676 B2 | 5/2012 | Greenberg et al. |
| 8,170,682 B2 | 5/2012 | Greenberg et al. |
| 8,180,453 B2 | 5/2012 | Greenberg et al. |
| 8,180,454 B2 | 5/2012 | Greenberg et al. |
| 8,180,460 B2 | 5/2012 | Nevsmith et al. |
| 8,190,267 B2 | 5/2012 | Greenberg et al. |
| 8,195,266 B2 | 6/2012 | Whalen, III et al. |
| 8,197,539 B2 | 6/2012 | Nasiatka et al. |
| 8,239,034 B2 | 8/2012 | Greenberg et al. |
| 8,244,362 B2 | 8/2012 | Yonezawa |
| 8,359,083 B2 | 1/2013 | Clark et al. |
| 8,428,740 B2 | 4/2013 | Gefen et al. |
| 8,532,497 B2 | 9/2013 | Chan et al. |
| 2001/0011844 A1 | 8/2001 | Ernst et al. |
| 2002/0091421 A1 | 7/2002 | Greenberg et al. |
| 2003/0023297 A1 | 1/2003 | Byers et al. |
| 2003/0032946 A1 | 2/2003 | Fishman et al. |
| 2003/0100823 A1 | 5/2003 | Kipke et al. |
| 2003/0132946 A1 | 7/2003 | Gold |
| 2003/0181957 A1 | 9/2003 | Greenberg et al. |
| 2003/0208248 A1 | 11/2003 | Carter et al. |
| 2004/0054407 A1 | 3/2004 | Tashiro et al. |
| 2004/0078064 A1 | 4/2004 | Suzuki |
| 2004/0080026 A1 | 4/2004 | Minamio et al. |
| 2004/0082981 A1 | 4/2004 | Chow et al. |
| 2004/0088026 A1 | 5/2004 | Chow et al. |
| 2004/0098067 A1 | 5/2004 | Ohta et al. |
| 2004/0181265 A1 | 9/2004 | Palanker et al. |
| 2004/0189940 A1 | 9/2004 | Kutschbach et al. |
| 2005/0015120 A1 | 1/2005 | Seibel et al. |
| 2005/0119605 A1 | 6/2005 | Sohn |
| 2005/0146954 A1 | 7/2005 | Win et al. |
| 2005/0168569 A1 | 8/2005 | Igarashi et al. |
| 2005/0226201 A1 | 10/2005 | McMillin |
| 2006/0106432 A1 | 5/2006 | Sawan et al. |
| 2006/0111757 A9 | 5/2006 | Greenberg et al. |
| 2006/0184245 A1 | 8/2006 | Graf et al. |
| 2006/0215049 A1 | 9/2006 | Sandini et al. |
| 2006/0282128 A1 | 12/2006 | Tai et al. |
| 2006/0287688 A1 | 12/2006 | Yonezawa |
| 2007/0005116 A1 | 1/2007 | Lo |
| 2007/0123766 A1 | 5/2007 | Whalen et al. |
| 2007/0142877 A1 | 6/2007 | McLean |
| 2007/0142878 A1 | 6/2007 | Krulevitch et al. |
| 2007/0191909 A1 | 8/2007 | Ameri et al. |
| 2008/0114230 A1 | 5/2008 | Addis |
| 2008/0234791 A1 | 9/2008 | Arle et al. |
| 2008/0262571 A1 | 10/2008 | Greenberg et al. |
| 2008/0288036 A1 | 11/2008 | Greenberg et al. |
| 2008/0288067 A1 | 11/2008 | Flood |
| 2008/0294224 A1 | 11/2008 | Greenberg et al. |
| 2009/0002034 A1 | 1/2009 | Westendorp et al. |
| 2009/0005835 A1 | 1/2009 | Greenberg et al. |
| 2009/0024182 A1 | 1/2009 | Zhang et al. |
| 2009/0118805 A1 | 5/2009 | Greenberg et al. |
| 2009/0192571 A1 | 7/2009 | Stett et al. |
| 2009/0204207 A1 | 8/2009 | Blum et al. |
| 2009/0204212 A1 | 8/2009 | Greenberg et al. |
| 2009/0216295 A1 | 8/2009 | Zrenner et al. |
| 2009/0228069 A1 | 9/2009 | Dai et al. |
| 2009/0287275 A1 | 11/2009 | Suaning et al. |
| 2009/0326623 A1 | 12/2009 | Greenberg et al. |
| 2010/0087895 A1 | 4/2010 | Zhou et al. |
| 2010/0174224 A1 | 7/2010 | Sohn |
| 2010/0204754 A1 | 8/2010 | Gross et al. |
| 2010/0249877 A1 | 9/2010 | Naughton |
| 2010/0249878 A1 | 9/2010 | McMahon et al. |
| 2010/0331682 A1 | 12/2010 | Stein et al. |
| 2011/0054583 A1 | 3/2011 | Litt et al. |
| 2011/0069962 A1 | 3/2011 | Castor et al. |
| 2011/0106229 A1 | 5/2011 | Ortmann |
| 2011/0135317 A1 | 6/2011 | Chaplin |
| 2011/0172736 A1 | 7/2011 | Gefen et al. |
| 2011/0254661 A1* | 10/2011 | Fawcett et al. ............... 340/5.61 |
| 2012/0035725 A1 | 2/2012 | Gefen et al. |
| 2012/0035726 A1 | 2/2012 | Gross et al. |
| 2012/0041514 A1 | 2/2012 | Gross et al. |
| 2012/0194781 A1 | 8/2012 | Agurok |
| 2012/0194871 A1 | 8/2012 | Murata |

(56) References Cited

U.S. PATENT DOCUMENTS

| | | | |
|---|---|---|---|
| 2012/0209350 A1 | 8/2012 | Taylor et al. | |
| 2012/0221103 A1 | 8/2012 | Liran et al. | |
| 2012/0259410 A1 | 10/2012 | Gefen et al. | |
| 2012/0268080 A1 | 10/2012 | Jeon et al. | |
| 2013/0108091 A1 | 5/2013 | Stoffaneller et al. | |
| 2013/0126713 A1* | 5/2013 | Haas et al. | 250/208.2 |
| 2013/0148828 A1 | 6/2013 | Fort et al. | |
| 2013/0322462 A1* | 12/2013 | Poulsen | 370/458 |
| 2014/0031931 A1 | 1/2014 | Liran et al. | |
| 2014/0047713 A1* | 2/2014 | Singh et al. | 29/869 |
| 2014/0143559 A1 | 5/2014 | Gefen et al. | |
| 2014/0188222 A1 | 7/2014 | Gefen et al. | |

FOREIGN PATENT DOCUMENTS

| | | |
|---|---|---|
| DE | 10315397 | 10/2004 |
| EP | 1355435 | 10/2003 |
| EP | 1848129 | 10/2007 |
| JP | 2000-350742 | 12/2000 |
| JP | 2003-528702 | 9/2003 |
| WO | WO0191854 | 12/2001 |
| WO | WO03032946 | 4/2003 |
| WO | WO2007006376 | 1/2007 |
| WO | WO2007009539 | 1/2007 |
| WO | 2007/076347 | 7/2007 |
| WO | WO2007095395 | 8/2007 |
| WO | WO2010035173 | 4/2010 |
| WO | WO2010089739 | 8/2010 |
| WO | WO2011086545 | 7/2011 |
| WO | WO 2011/163262 A2 | 12/2011 |
| WO | 2012/017426 | 2/2012 |
| WO | 2012/092209 | 7/2012 |
| WO | 2012/114327 | 8/2012 |
| WO | WO/2012/153325 | 11/2012 |
| WO | WO 2014/080343 | 5/2014 |
| WO | WO 2014/141089 | 9/2014 |

OTHER PUBLICATIONS

An Office Action dated Mar. 3, 2015, which issued during the prosecution of U.S. Appl. No. 13/148,461.
An Office Action dated Feb. 5, 2015, which issued during the prosecution of U.S. Appl. No. 14/199,462.
An Office Action dated Apr. 14, 2015, which issued during the prosecution of U.S. Appl. No. 14/018,850.
An Office Action dated Feb. 3, 2014, which issued during the prosecution of U.S. Appl. No. 13/683,158.
An invitation to pay additional fees that issued in PCT/IB2014/067417.
An invitation to pay additional fees that issued in PCT/IB2015/050224.
An EP search report dated Feb. 20, 2015 that issued in EP 12782462.1.
Delbruck et al.: "Analog VLSI Adaptive, Logarithmic, Wide-Dynamic-Range Photoreceptor," 1994 International Symposium on Circuits and Systems (London, 1994), p. 339-342.
Grill W., at al., Implanted Neural Interfaces: Biochallenges and Engineered Solutions, Annu. Rev. Biomed. Eng. 2009, 11:1.
Jourdain R P., at al., "Fabrication of piezoelectric thick-film bimorph micro-actuators from bulk ceramics using batch-scale methods" Multi-Material Micro Manufacture, S. Dimov and W. Menz (Eds.) 2008 Cardiff University, Cardiff, UK., Whittles Publishing Ltd.
Kim B., "Through-Silicon-Via Copper Deposition for Vertical Chip Integration" Master. Res, Soc. Symp. Proc. vol. 970, 2007 Material Research Society.
Lianga C, at al., "Surface modification of cp-Ti using femtosecond laser micromachining and the deposition of Ca/P layer" Materials Letters vol. 62, Issue 23, Aug. 31, 2008, pp. 3783-3786—an abstract.
David C Ng, et al., "Pulse frequency modulation based CMOS image sensor for subretinal stimulation" IEEE Transactions on Circuits and Systems—II: Express Briefs, vol. 53, No. 6, Jun. 2006.

News Release—Sony develops back-illuminated CMOS image sensor, realizing high picture quality, nearly twofold sensitivity (*1) and low noise, Jun. 2008 http://www.sony.net/SonyInfo/News/Press/200806/08-069E/index.html.
Puech M., et al., "Fabrication of 3D packaging TSV using DRIE" ALCATEL Micro Machining Systems, vvww.adixen.com, Mar. 2007.
Seo J M., et al., "Biocompatibility of polyimide microelectrode array for retinal stimulation," Materials Science and Engineering: C, vol. 24, No. 1, Jan. 5, 2004, pp. 185-189(5).
Sorkin R., et al., "Process entanglement as a neuronal anchorage mechanism to rough surfaces," Nanotechnology 20 (2009) 015101 (8pp).
Starzyk JA, et al., "A DC-DC charge pump design based on voltage doublers" IEEE Transaction on Circuits and Systems—I: Fundamental theory and applications, vol. 48, No. 3 Mar. 2001.
Stein DJ, et al., "High voltage with Si series photovoltaics" Proceedings of SPE, the International Society for Optical Engineering 2006, vol. 6287, pp. 62870D.1-62870D, (an abstract).
Swain P K., et al., "Back-Illuminated Image Sensors Come to the Forefront. Novel materials and fabrication methods increase quality and lower cost of sensors for machine vision and industrial imaging." Photonics Spectra Aug. 2008.
Vorobyeva A Y. at al., "Metallic light absorbers produced by femtosecond laser pulses," Advances in Mechanical Engineering vol. 2010, Article ID 452749, 4 pages doi:10.1155/2010/452749, Hindawi Publishing Corporation.
Vorobyeva A Y. et al., "Femtosecond laser structuring of titanium implants," Applied Surface Science vol. 253, Issue 17, Jun. 30, 2007, pp. 7272-7280—an abstract.
Wallman L., et al., "The geometric design of micromachined silicon sieve electrodes influences functional nerve regeneration," Biomaterials May 2001:22(10):1 187-93, (an abstract).
Walter P., et al., "Cortical Activation via an implanted wireless retinal prosthesis," Investigative Ophthalmology and Visual Science. 2005;46:1780-1785.
Wu J T. and Chang K L., "MOS charge pumps for low-voltage operation" IEEE Journal of Solid-State Circuits, vol. 33 No. 4 Apr. 1998.
Zrenner E., 2002. "Will retinal implants restore vision?" Science 295(5557), pp. 1022-1025.
Office Action dated Aug. 24, 2011 issued during the prosecution of related U.S. Appl. No. 12/368,150.
International Preliminary Report on Patentability and Written Opinion dated Aug. 9, 2011, issued in related International Application No. PCT/IL2010/000097.
International Search Report dated Aug. 17, 2010, issued in related International Application No. PCT/IL2010/000097.
International Search Report and Written Opinion dated Aug. 12, 2011, issued in related International Application No. PCT/IL2011/000022.
International Search Report and Written Opinion dated Dec. 12, 2011 issued in related International Application No. PCT/IL2011/00609.
An Office Action dated Aug. 28, 2012, which issued during the prosecution of U.S. Appl. No. 12/852,218.
An Office Action dated Sep. 28, 2012, which issued during the prosecution of U.S. Appl. No. 13/103,264.
An International Preliminary Report on Patentability dated Jul. 17, 2012, which issued during the prosecution of Applicant's PCT/IL2011/000022.
A Supplementary European Search Report dated Aug. 10, 2012, which issued during the prosecution of Applicant's European Application No. 10 73 8277.
Palanker D. et al., "Design of a high-resolution optoelectric retinal prosthesis". Journal of Neural Engineering, Institute of physics publishing, Bristol, GB. vol. 2, No. 1, Mar. 1, 2005, pp. S105-S120, XP002427333, ISSN: 17412552, DOI: 10.1088/1741-2560/2/1/012.
Cortical Visual Neuro-Prosthesis for the Blind: Retina-Like Software/Hardware Preprocessor, F.J. Pelayol, A. Martinezl, S. Romerol, Ch.A. Morillasl, E. Rosl , E. Fernandez2 1Dept. of Computer Architecture and Technology, University of Granada, Spain 2Dept. of Histology and Institute of Bioengineering, University Miguel Hernandez, Alicante, Spain Neural Engineering, 2003. Conference Proceedings. First International IEEE EMBS Conference.

(56) References Cited

OTHER PUBLICATIONS

"Single-Chip CMOS Image Sensors for a Retina Implant System", Markus Schwarz, Ralf Hauschild, Bedrich J. Hosticka, Senior Member, IEEE, Jurgen Huppertz, Student Member, IEEE, Thorsten Kneip, Member, IEEE, Stephan Kolnsberg, Lutz Ewe, and Hoc Khiem Trieu, 2000.

An International Search Report dated Aug. 12, 2011, which issued during the prosecution of Applicant s PCT/IL2011/000022.

An International Search Report and a Written Opinion both dated Sep. 17, 2012, which issued during the prosecution of Applicant's PCT/IL12/00057.

Schwarz et al. "Hardware Architecture of a Neural Net Based Retina Implant for Patients Suffering from Retinitis Pigmentosa," Fraunhofer Institute of Microelectronic Circuits and Systems, pp. 653-658 (1996).

Ganesan et al. "Diamond Penetrating Electrode Array for Epi-Retinal Prosthesis," 32nd Annual International Conference of the IEEE EMBS, pp. 6757-6760 (2010).

Finn, et al. "An Amphibian Model for Developing and Evaluating Retinal Protheses," 18th Annual International Conference of the IEEE Engineering in Medicine and Biology Society, pp. 1540-1541 (1996).

Shawn Kelly, "A System for Electrical Retinal Stimulation for Human Trials," Massachusetts Institute of Technology, pp. 1-45 (1998).

Andreou et al. "Analog Integrated Circuits and Signal Processing," An International Journal, vol. 9, No. 2, pp. 141-166 (1996).

Office Action for U.S. Appl. No. 13/034,516 dated Dec. 14, 2012.

Office Action for U.S. Appl. No. 12/687,509 dated Dec. 7, 2012.

Office Action for U.S. Appl. No. 13/148,461 dated Mar. 13, 2013.

Office Action for U.S. Appl. No. 12/687,509 dated Jun. 6, 2013.

International Search Report and Written Opinion for International Application No. PCT/IL2012/000186 dated Sep. 4, 2012.

Humayun et al. Visual perception in a blind subject with a chronic microelectronic retinal prosthesis, Vision Research, vol. 43, pp. 2573-2581 (2003).

Tran et al. "A Fully Flexible Stimulator using 65 nm CMOS Process for 1024-electrode Epi-retinal Prosthesis," 31st Annual International Conference of the IEEE EMBS, pp. 1643-1646 (2009).

Office Action issued in U.S. Appl. No. 13/437,310, dated Aug. 12, 2013.

An interview summary in U.S. Appl. No. 13/437,310 dated Nov. 14, 2013 in connection with the Office Action issued on Aug. 12, 2013.

European Search Report for European Application No. EP11732733 dated Jul. 16, 2013.

Yoo et al. "Excimer laser deinsulation of Parylene-C on iridium for use in an activated iridium oxide film-coated Utah electrode array," Journal of Neuroscience Methods, 215 (2013) 78-87.

Official Action dated Oct. 22, 2013, which issued during the prosecution of Applicant's U.S. Appl. No. 13/148,461.

Extended European Search Report dated Nov. 19, 2013 which issued during the prosecution of Applicant's European Patent Application No. 11814197.7.

J.F. Rizzo, "Methods and Perceptual Thresholds for Short-Term Electrical Stimulation of Human Retina with Microelectrode Arrays", Investigative Ophthalmology and Visual Science, vol. 44, No. 12, (Dec. 1, 2003) pp. 5355-5361.

Normann et al., "High-resolution spatio-temporal mapping of visusal pathways using multi-electrode arrays," Vision Research 41 (2001) 1261-1275.

Notice of Allowance issued in U.S. Appl. No. 13/437,310, dated Jan. 28, 2014.

Weber et al., "Implementations and implications of foveated vision", Recent Patents on Computer Science 2009, 2 75-85.

Schmidhuber et al., "Learning to generate artificial fovea trajectories for target detection", International Journal of Neural Systems, [1991] 2(1 & 2): 135-141.

Park et al., "A foveated-structured CMOS retina chip for edge detection with local light adaptation", Sensors and Actuators A 108 [2003] 75-80.

Partial ISR, dated Jun. 16, 2014, which issued in the Applicant's PCT Application No. PCT/IB2014/059672.

Examination Report, dated Apr. 16, 2014, which issued in EP11732733.8.

JP Office Action, dated Nov. 27, 2013, for JP 2011-548843.

Examination Report, dated Feb. 26, 2014 which issued in EP10738277.2.

The ISR and the Written Opinion issued on Jun. 30, 2015 in PCT/IB2014/067417.

The ISR and the Written Opinion issued on Jun. 30, 2015 in PCT/IB2015/050224.

The office action as issued in U.S. Appl. No. 13/827,919 on Aug. 10, 2015.

* cited by examiner

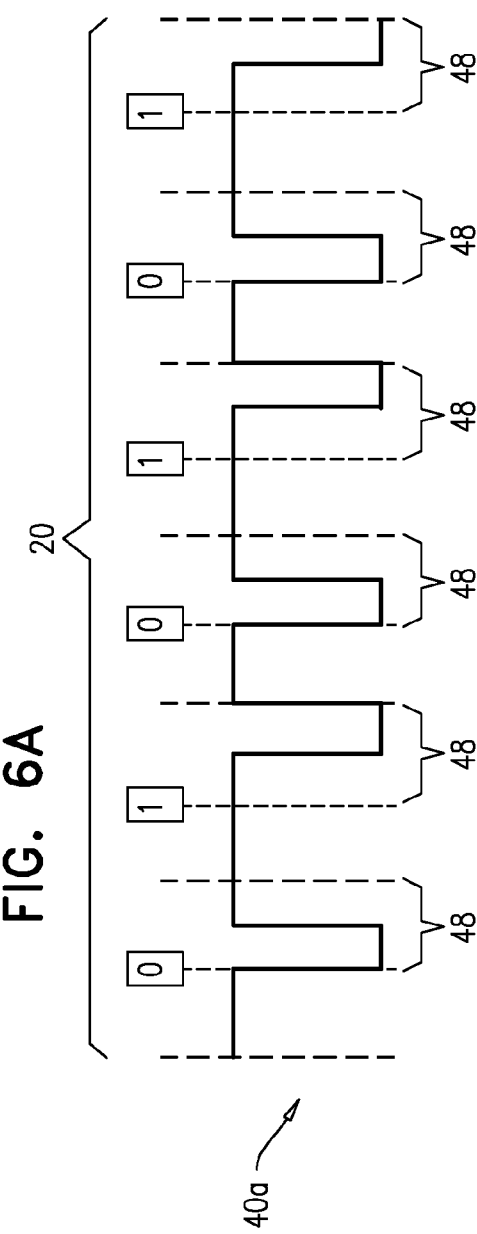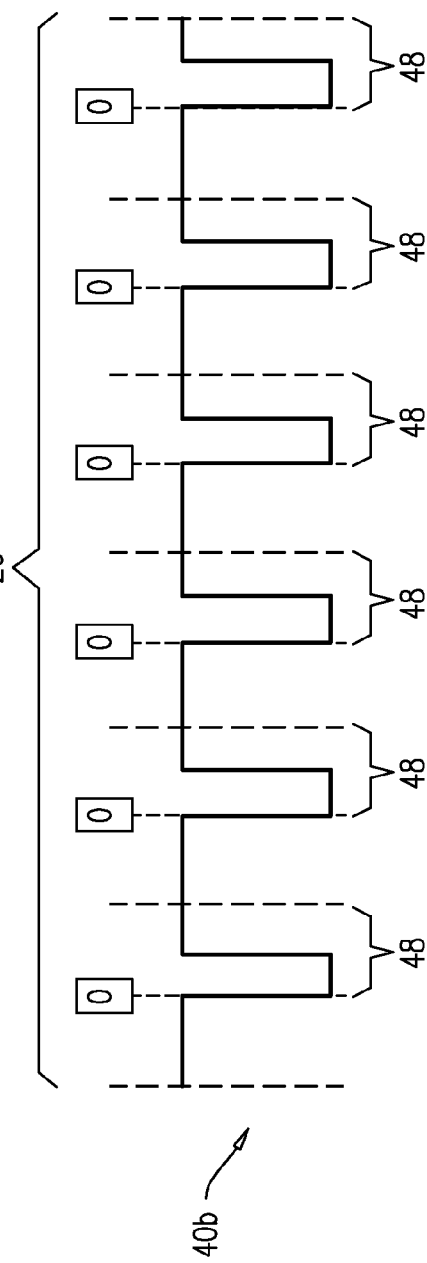

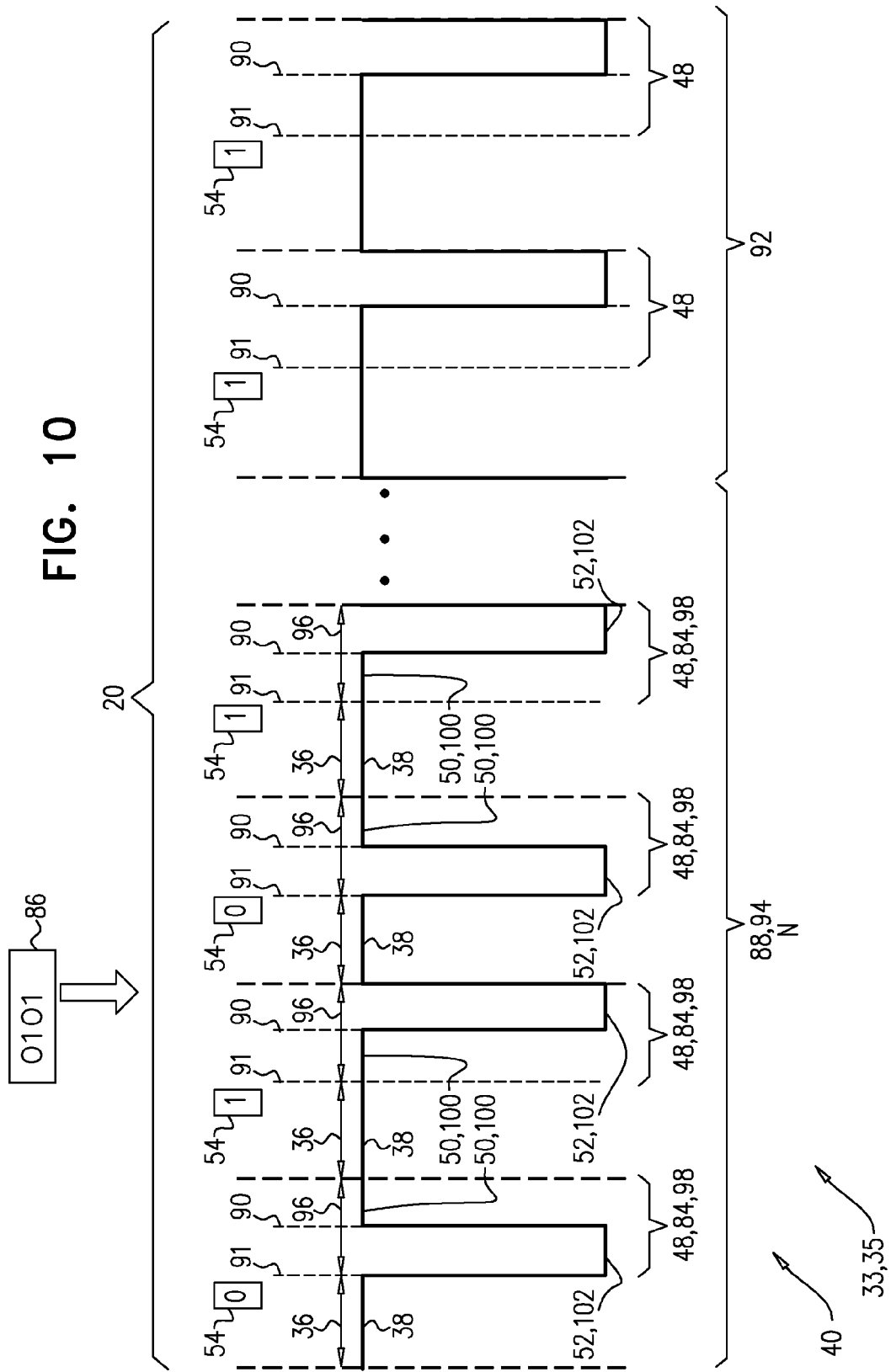

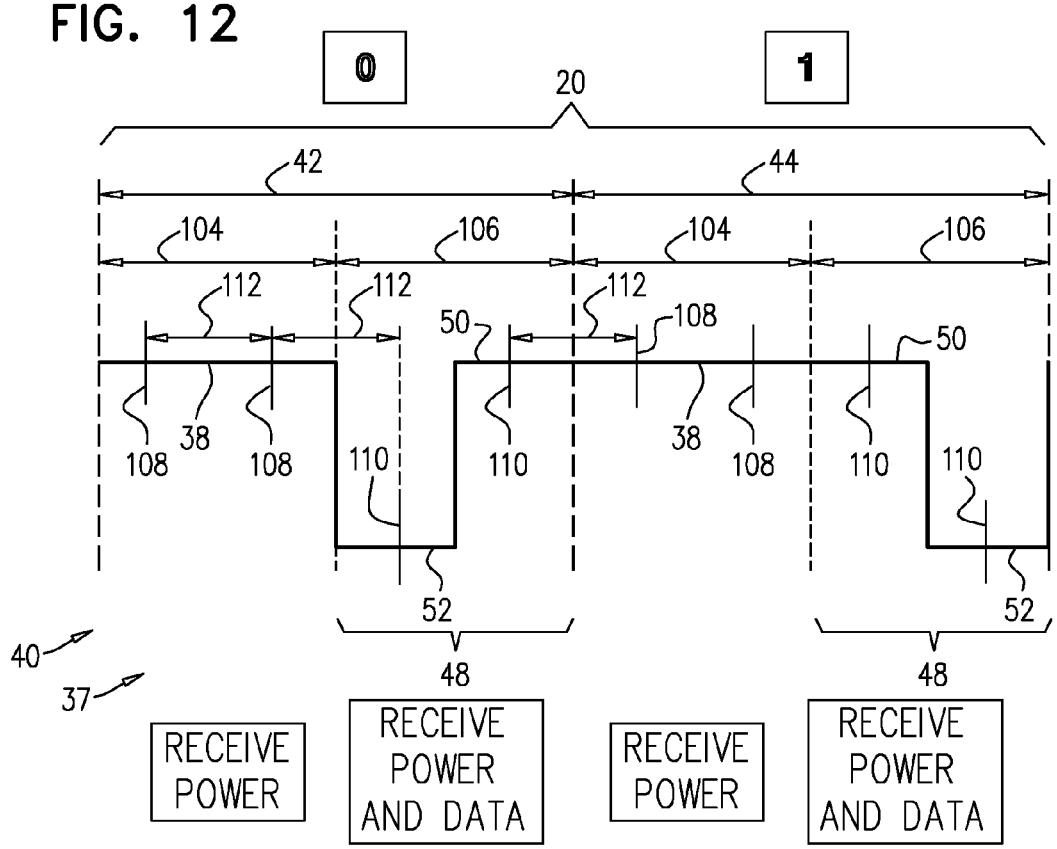
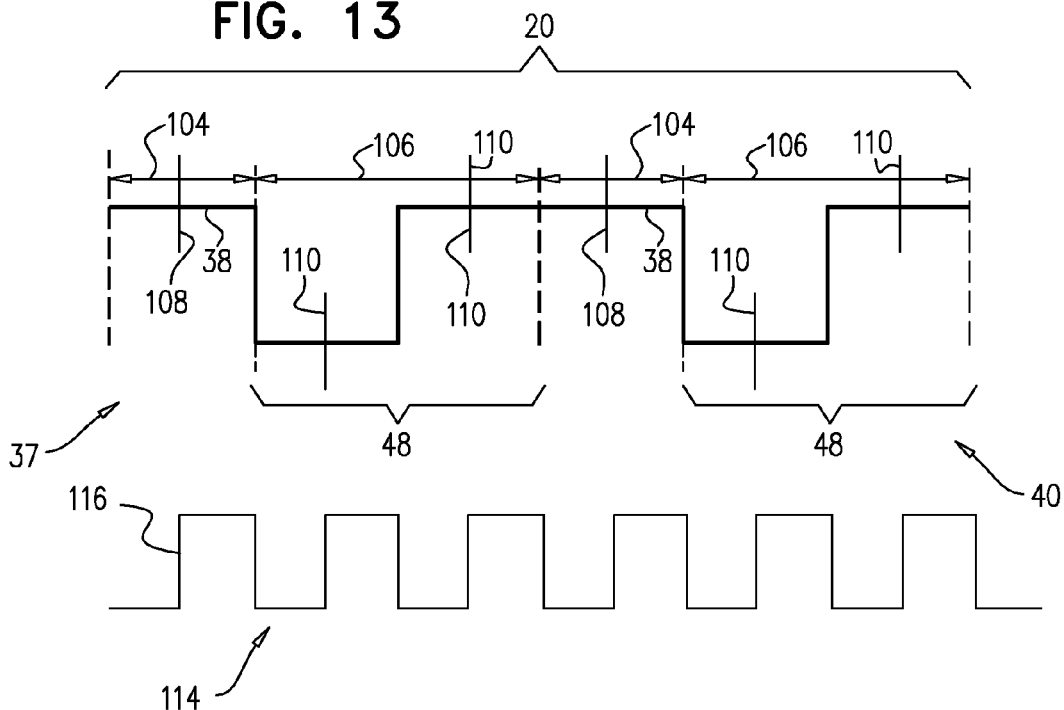

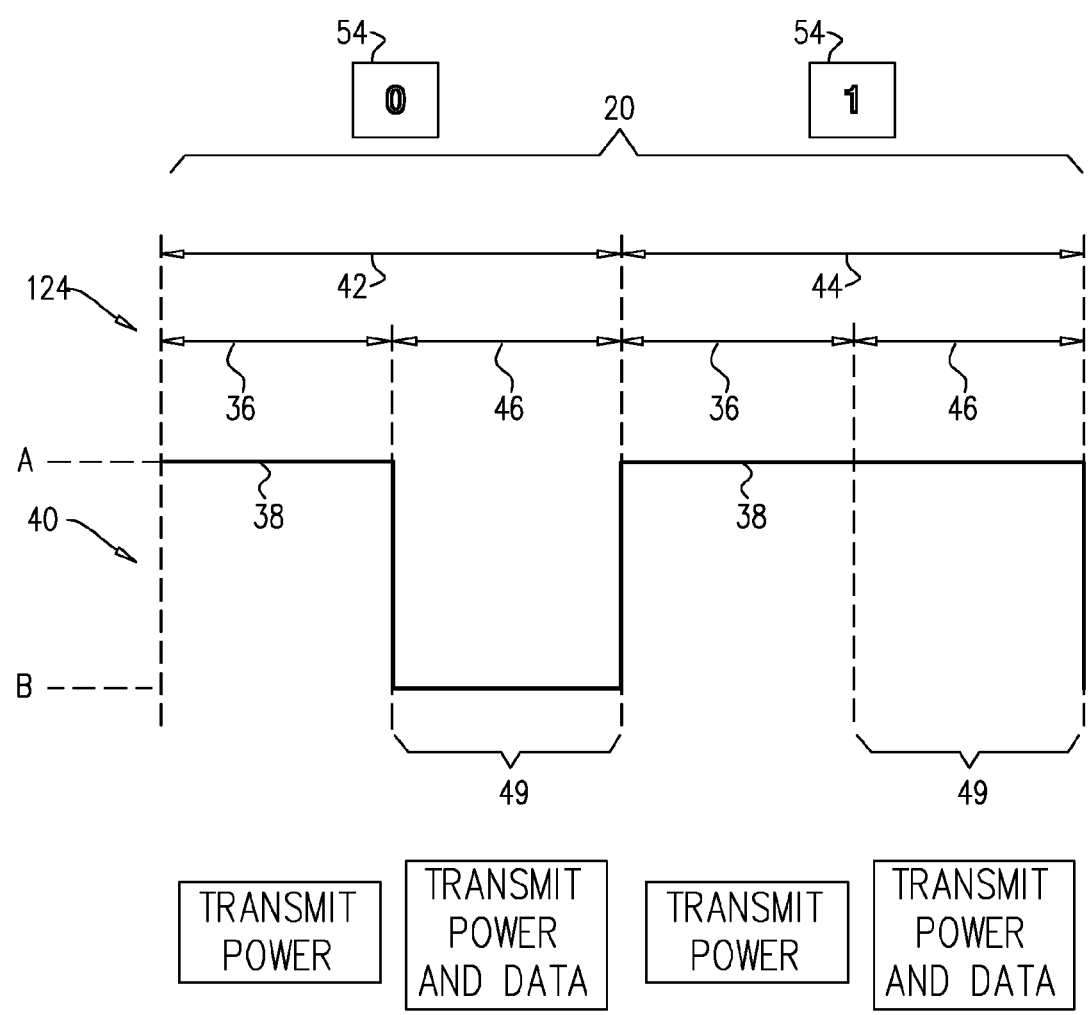

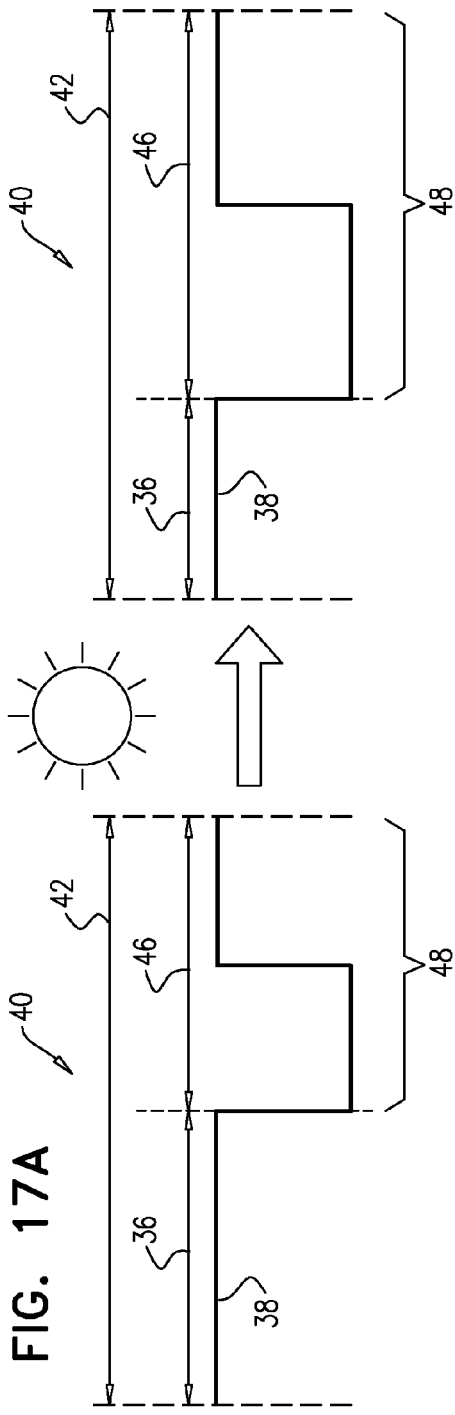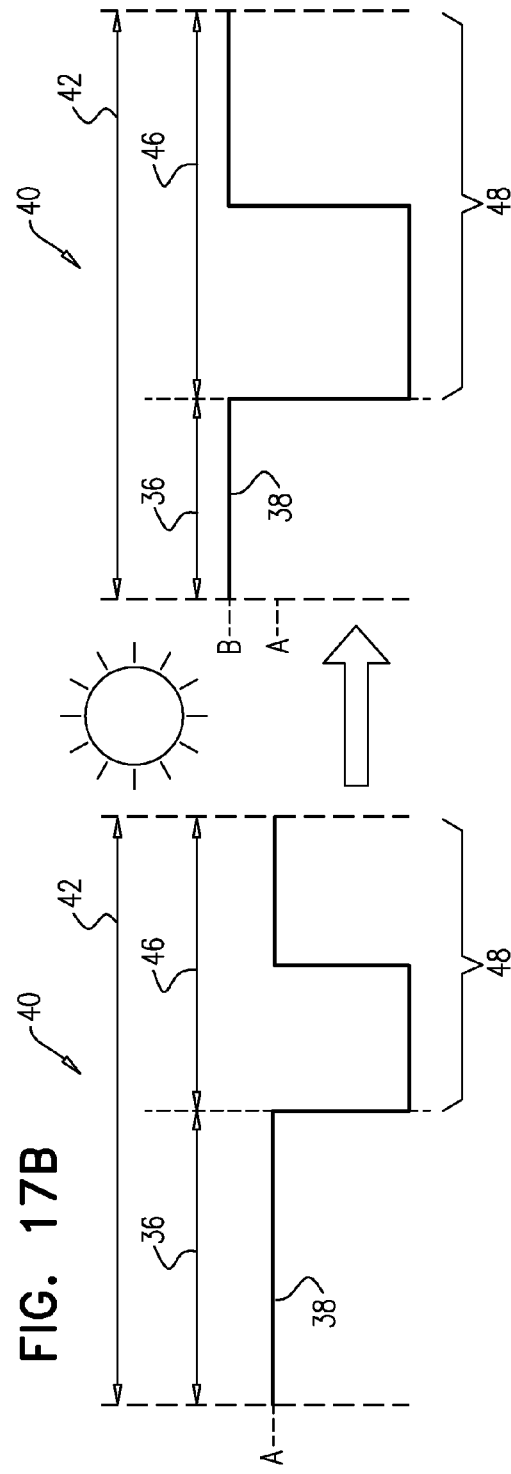

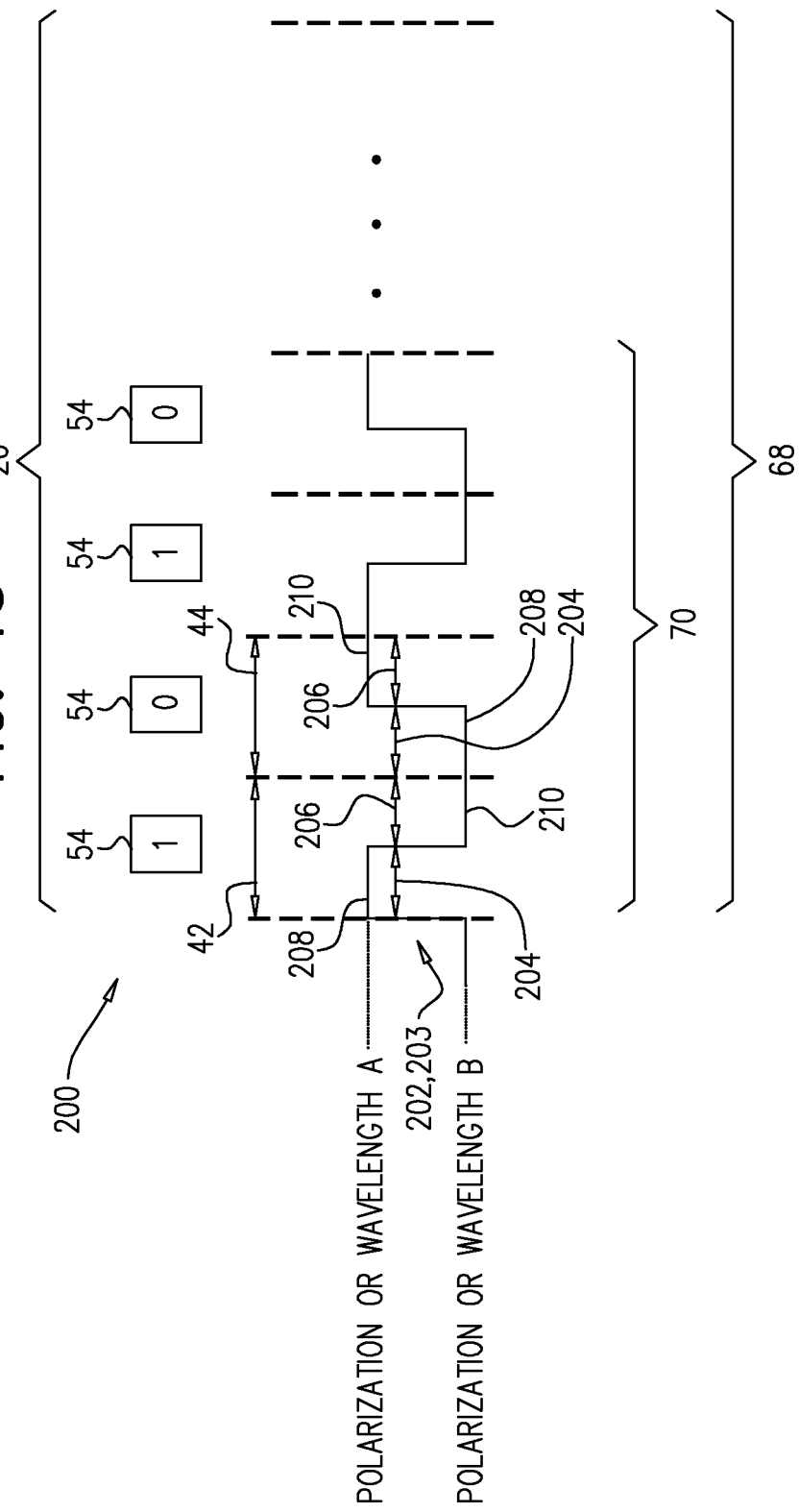

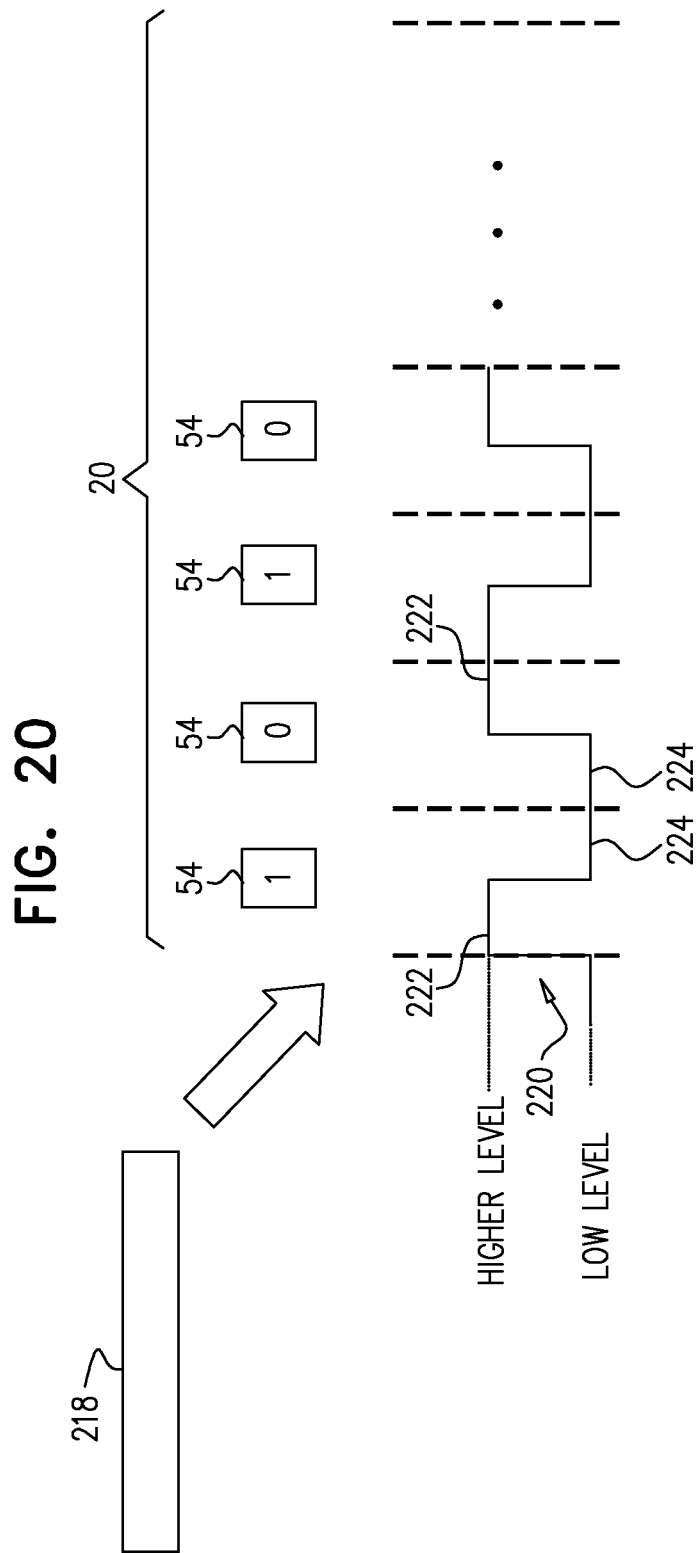

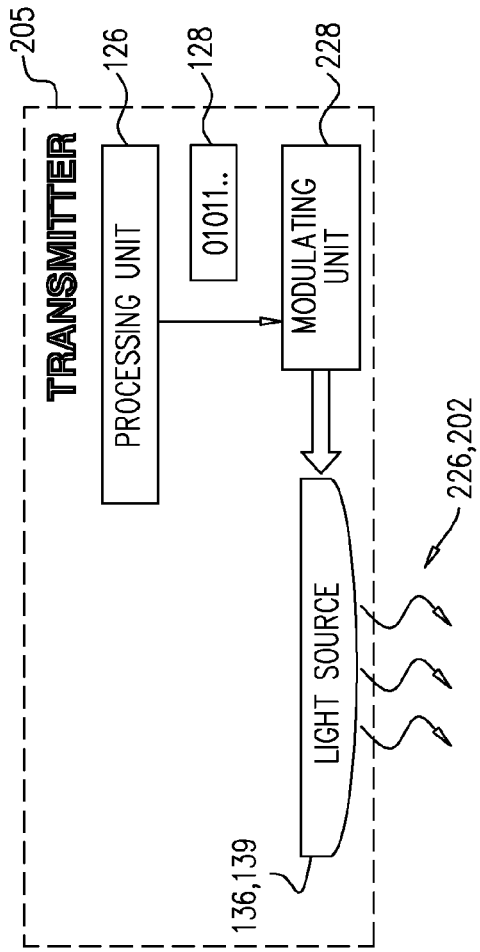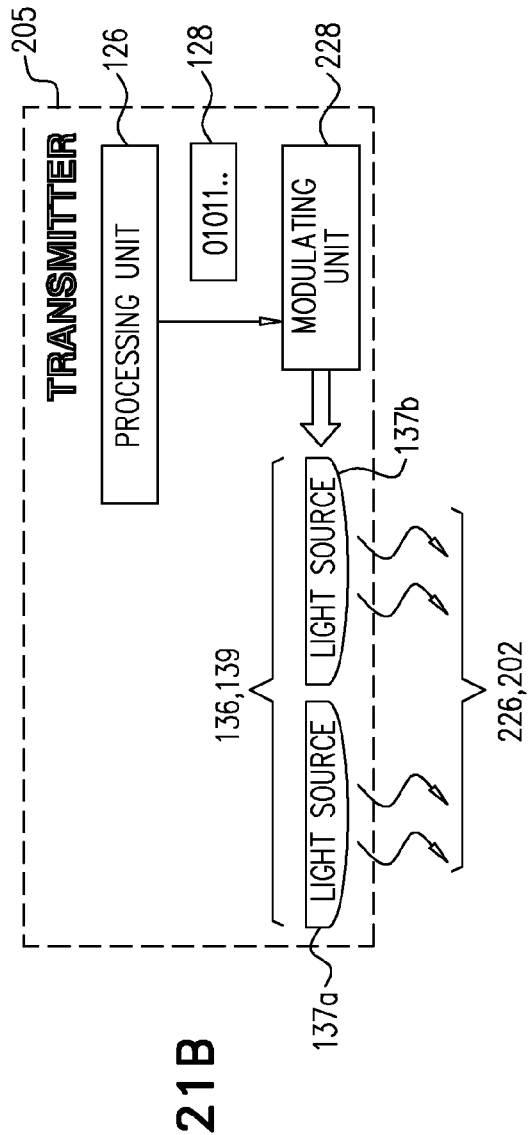
FIG. 21A
FIG. 21B

TRANSFER OF POWER AND DATA

FIELD OF THE INVENTION

The present invention relates generally to transfer of power and data. Specifically, it relates to apparatus and methods for transmission of power and data to a device, e.g., a retinal prosthesis device.

BACKGROUND OF THE INVENTION

Retinal malfunction is a leading cause of blindness and visual impairment. Implantation of a retinal prosthesis in the eye may be helpful in restoring some vision to individuals suffering from blindness of retinal origin. A variety of retinal prostheses have been described in the patent literature.

U.S. Pat. No. 8,150,526 to Gross, which is incorporated herein by reference, describes apparatus including an external device, including a mount, which is placed in front of an eye of a subject. A laser is coupled to the mount and configured to emit toward the eye radiation that is outside of 380-750 nm. A partially-transparent mirror is coupled to the mount. An intraocular device is implanted entirely in the subject's eye, and includes a plurality of stimulating electrodes, and an energy receiver, which receives the radiation from the laser and generates a voltage drop in response thereto. A plurality of photosensors detect photons and generate a signal in response thereto. Driving circuitry is coupled to the energy receiver and to the photosensors, and receives the signals from the photosensors and utilizes the voltage drop to drive the electrodes to apply currents to the retina in response to the signals from the photosensors. Other embodiments are also described.

U.S. Pat. No. 8,428,740 to Gefen, which is incorporated herein by reference, describes apparatus including an external device including a mount, which is placed in front of an eye of a subject. A power source is coupled to the mount and emits energy toward the eye. An intraocular device is implanted entirely in the subject's eye, and includes a control unit, a plurality of stimulating electrodes, and an energy receiver, which receives the energy from the power source and generates a voltage drop in response. A plurality of photosensors detect photons and generate a signal in response. Driving circuitry is coupled to the energy receiver and to the photosensors, and drives the electrodes to apply electrical charges to a retina in response to the signals from the photosensors. The external device modulates the emitted energy, and the control unit demodulates the modulated energy to regulate an operation parameter of the intraocular device. Other embodiments are also described.

U.S. Pat. No. 8,442,641 to Gross, which is incorporated herein by reference, describes apparatus for use with an external non-visible light source. The apparatus comprises an intraocular device configured for implantation in a human eye, and comprising an energy receiver. The energy receiver is configured to receive light emitted from the external non-visible light source, and extract energy from the emitted light for powering the intraocular device. The intraocular device is configured to regulate a parameter of operation of the intraocular device based on a modulation of the light emitted by the external non-visible light source and received by the energy receiver. Other embodiments are also described.

US Patent Application 2011/0172736 to Gefen, which is incorporated herein by reference, describes apparatus configured for implantation in a body of a subject. The apparatus includes a support substrate, and at least 500 electrodes protruding at least 50 um from the support substrate, each electrode having (a) a distal tip, (b) an electrically-exposed tip portion, and (c) a cross-section of 50-1500 um2, 20 um from the distal tip. Other embodiments are also described.

US Patent Application 2012/0041514 to Gross, which is incorporated herein by reference, describes an external device including a mount, which is placed in front of a subject's eye. A laser is coupled to the mount and emits radiation that is outside of 380-750 nm. A partially-transparent mirror is coupled to the mount. An intraocular device is implanted entirely in the subject's eye, and includes a plurality of stimulating electrodes, and an energy receiver, which receives the radiation from the laser and generates a voltage drop. A plurality of photosensors detect photons and generate a signal. Driving circuitry is coupled to the energy receiver and to the photosensors, and receives the signals from the photosensors and utilizes the voltage drop to drive the electrodes to apply currents to the retina in response to the signals from the photosensors. Other embodiments are also described.

US Patent Application 2012/0221103 to Liran, which is incorporated herein by reference, describes a medical device including an array of electrodes, configured for implantation in contact with tissue in an eye of a living subject. Driver circuitry is configured to drive the electrodes in an alternating pattern, such that different groups of the electrodes are driven to stimulate the tissue during different, predetermined respective time periods. A power sensor may be coupled to deactivate a first group of the electrodes when the available electrical power drops below a predetermined threshold, while a second group of the electrodes remains active. Other embodiments are also described.

US Patent Application 2012/0259410 to Gefen, which is incorporated herein by reference, describes apparatus for use with an external non-visible light source. The apparatus comprises an intraocular device configured for implantation in a human eye, and comprising an energy receiver. The energy receiver is configured to receive light emitted from the external non-visible light source, and extract energy from the emitted light for powering the intraocular device. The intraocular device is configured to regulate a parameter of operation of the intraocular device based on a modulation of the light emitted by the external non-visible light source and received by the energy receiver. Other embodiments are also described.

SUMMARY OF THE INVENTION

Certain battery-less devices, such as the retinal prostheses described in the Background section of the present patent application, typically require almost-continual powering in order to remain functional. In some applications, wireless power transfer, e.g., via transmitted light, is the preferred method of powering the device. Typically, infrared (IR) light is used to power the retinal prostheses described in the Background, since IR light is not visible and therefore does not interfere with the subject's vision (i.e., it is not detected by native photosensors of the subject).

In addition to utilizing the transfer of power, these devices may also utilize periodic transfer of data. For example, a user of a retinal prosthesis may periodically adjust a setting such as a desired contrast, and this setting must be communicated to the device. Applications of the present invention address the challenge of communicating data to the device without interrupting the flow of power, i.e., transmitting both power and data effectively simultaneously.

In accordance with some applications of the present invention, the present patent application describes a method for transmission of power and data during a plurality of consecutive time intervals. Each time interval contains both a power-transmission portion and a power-and-data-transmission portion. During the power-transmission portion of each of the intervals, a power signal is transmitted. The power signal does not encode data, and is generally used only to power the receiving device. During the power-and-data-transmission portion of each of the intervals, a power-and-data signal is transmitted. The power-and-data signal encodes a single bit, and typically includes both a high-level portion and a low-level portion.

To help maintain sufficient transfer of power to the receiving device, the transmission duty cycle in each of the consecutive time intervals is typically configured to be independent of the transmitted data, and is further typically configured to be between 65% and 90%.

There is therefore provided, in accordance with some applications of the present invention, a method for transmission of power and data during a plurality of consecutive time intervals, the method including:

during a power-transmission portion of each of the plurality of consecutive time intervals, transmitting a power signal in which no data is encoded; and during a power-and-data-transmission portion of each of the plurality of consecutive time intervals, transmitting a power-and-data signal in which is encoded a single bit, the power-and-data signal including: (a) a high-level power-and-data signal portion, and (b) a low-level power-and-data signal portion.

In some applications, respective durations of (a) the high-level power-and-data signal portion, and (b) the low-level power-and-data signal portion, are the same as each other, during each of the plurality of consecutive time intervals.

In some applications, the method further includes configuring respective transmission duty cycles in each of at least eight consecutive ones of the plurality of consecutive time intervals to be the same as each other.

In some applications, the method further includes configuring respective transmission duty cycles in each of at least four consecutive ones of the plurality of consecutive time intervals to be the same as each other.

In some applications, the method further includes configuring respective durations of the power-transmission portion in each of at least eight consecutive ones of the plurality of consecutive time intervals to be the same as each other. In some applications, the method further includes configuring respective durations of the power-and-data-transmission portion in each of the at least eight consecutive ones of the plurality of consecutive time intervals to be the same as each other.

In some applications, the method further includes configuring respective durations of the power-transmission portion in each of at least four consecutive ones of the plurality of consecutive time intervals to be the same as each other.

In some applications, the method further includes configuring respective durations of the power-and-data-transmission portion in each of the at least four consecutive ones of the plurality of consecutive time intervals to be the same as each other.

In some applications, the method further includes configuring a transmission duty cycle in each of the plurality of consecutive time intervals to be independent of the data.

In some applications, the method further includes configuring the transmission duty cycle in each of the plurality of consecutive time intervals to be dependent on a parameter that is independent of the data.

In some applications, the method further includes sensing the parameter and configuring the transmission duty cycle in each of the plurality of consecutive time intervals to be dependent on the sensed parameter.

In some applications, sensing includes sensing a level of ambient light, and configuring the transmission duty cycle to be dependent on the sensed parameter includes configuring the transmission duty cycle to be dependent on the sensed level of ambient light.

In some applications, sensing the level of ambient light includes sensing a level of ambient infrared light, and configuring the transmission duty cycle to be dependent on the sensed level of ambient light includes configuring the transmission duty cycle to be dependent on the sensed level of ambient infrared light.

In some applications, sensing the level of ambient light includes sensing a level of ambient visible light, and configuring the transmission duty cycle to be dependent on the sensed level of ambient light includes configuring the transmission duty cycle to be dependent on the sensed level of ambient visible light.

In some applications, configuring the transmission duty cycle to be dependent on the sensed level of ambient light includes configuring the transmission duty cycle to be inversely related to the sensed level of ambient light.

In some applications, the method further includes configuring (i) a maximum amplitude of the power signal, and (ii) a maximum amplitude of the power-and-data signal, in each of the plurality of consecutive time intervals, to be independent of the data.

In some applications, the method further includes configuring the maximum amplitudes in each of the plurality of consecutive time intervals to be dependent on a parameter that is independent of the data.

In some applications, the method further includes sensing the parameter and configuring the maximum amplitudes in each of the plurality of consecutive time intervals to be dependent on the sensed parameter.

In some applications, sensing includes sensing a level of ambient light, and configuring the maximum amplitudes to be dependent on the sensed parameter includes configuring the maximum amplitudes to be dependent on the sensed level of ambient light.

In some applications, sensing the level of ambient light includes sensing a level of ambient infrared light, and configuring the maximum amplitudes to be dependent on the sensed level of ambient light includes configuring the maximum amplitudes to be dependent on the sensed level of ambient infrared light.

In some applications, sensing the level of ambient light includes sensing a level of ambient visible light, and configuring the maximum amplitudes to be dependent on the sensed level of ambient light includes configuring the maximum amplitudes to be dependent on the sensed level of ambient visible light.

In some applications, configuring the maximum amplitudes to be dependent on the sensed level of ambient light includes configuring the maximum amplitudes to increase in response to an increased sensed level of ambient light.

In some applications, the method further includes configuring a transmission duty cycle in each of the plurality of consecutive time intervals to be fixed at exactly one value.

In some applications, transmitting the power-and-data signal includes transmitting the power-and-data signal with a duty cycle that is independent of the data.

In some applications, the plurality of consecutive time intervals include at least eight consecutive time intervals, and transmitting the power signal during the power-transmission portion of each of the plurality of consecutive time intervals includes transmitting the power signal during the power-transmission portion of each of the at least eight consecutive time intervals.

In some applications, the plurality of consecutive time intervals include at least four consecutive time intervals, and transmitting the power signal during the power-transmission portion of each of the plurality of consecutive time intervals includes transmitting the power signal during the power-transmission portion of each of the at least four consecutive time intervals.

In some applications, the method further includes configuring a transmission duty cycle in each of the plurality of consecutive time intervals to be n/(n+1), n being an integer greater than one.

In some applications, the method further includes configuring a transmission duty cycle in each of the plurality of consecutive time intervals to be between 65% and 90%.

In some applications, configuring the transmission duty cycle includes configuring the transmission duty cycle in each of the plurality of consecutive time intervals to be two thirds.

In some applications, configuring the transmission duty cycle includes configuring the transmission duty cycle in each of the plurality of consecutive time intervals to be three fourths.

In some applications, transmitting the power signal includes wirelessly transmitting the power signal, and transmitting the power-and-data signal includes wirelessly transmitting the power-and-data signal.

In some applications, wirelessly transmitting the power signal includes wirelessly transmitting the power signal using infrared transmission of the power signal, and wirelessly transmitting the power-and-data signal includes wirelessly transmitting the power-and-data signal using infrared transmission of the power-and-data signal.

In some applications, wirelessly transmitting the power signal using infrared transmission of the power signal includes transmitting the power signal from an infrared transmitter, and wirelessly transmitting the power-and-data signal using infrared transmission of the power-and-data signal includes transmitting the power-and-data signal from the infrared transmitter.

In some applications:
transmitting the power signal from the infrared transmitter includes transmitting the power signal from a transmitting element selected from the group consisting of: a light-emitting diode, and a laser, and
transmitting the power-and-data signal from the infrared transmitter includes transmitting the power-and-data signal from the selected transmitting element.

In some applications, transmitting the power-and-data signal includes transmitting an amplitude-modulated signal.

In some applications, transmitting the amplitude-modulated signal includes transmitting an amplitude-shift-keyed signal.

In some applications, transmitting the amplitude-shift-keyed signal includes transmitting an on-off encoded signal.

In some applications, transmitting the on-off encoded signal includes transmitting a Manchester encoded signal.

In some applications, for each of the plurality of consecutive time intervals:
the power transmission portion is a time sub-interval, a length of which is between 30% and 80% of a length of the time interval, and transmitting the power signal during the power-transmission portion includes transmitting the power signal during the time sub-interval.

In some applications:
the power-and-data signal includes a synchronization signal, in which is encoded a bit from a synchronization sequence of bits, during at least some of the plurality of consecutive time intervals, and
transmitting the power-and-data signal includes transmitting the synchronization signal.

In some applications:
the power-and-data signal includes the synchronization signal during at least sixteen consecutive ones of the plurality of consecutive time intervals, and
transmitting the synchronization signal includes transmitting the synchronization signal during the at least sixteen consecutive ones of the plurality of consecutive time intervals.

There is further provided, in accordance with some applications of the present invention, a method for transmission of power and synchronization-data during a plurality of consecutive time intervals, the method including:
during a power-transmission portion of each of the plurality of consecutive time intervals, transmitting a power signal in which no data is encoded; and
during a power-and-synchronization-data-transmission portion of each of the plurality of consecutive time intervals, transmitting a power-and-synchronization-data signal in which is encoded a single bit from a synchronization sequence of bits, the power-and-synchronization-data signal including: (a) a high-level power-and-synchronization-data signal portion, and (b) a low-level power-and-synchronization-data signal portion.

There is further provided, in accordance with some applications of the present invention, a method for receiving power and data during a plurality of consecutive time intervals, the method including:
during a power-receiving portion of each of the plurality of consecutive time intervals, receiving a power signal in which no data is encoded; and
during a power-and-data-receiving portion of each of the plurality of consecutive time intervals, receiving a power-and-data signal in which is encoded a single bit, the power-and-data signal including: (a) a high-level power-and-data signal portion, and (b) a low-level power-and-data signal portion.

In some applications, during each of the plurality of consecutive time intervals, (a) receiving the power-and-data signal includes sampling the power-and-data signal exactly 2N times, and (b) receiving the power signal includes sampling the power signal exactly N times.

In some applications, during each of the plurality of consecutive time intervals, (a) receiving the power-and-data signal includes sampling the power-and-data signal exactly N times, and (b) receiving the power signal includes sampling the power signal exactly N times, N being an even integer greater than one.

In some applications, receiving the power-and-data signal includes sampling the power-and-data signal by a receiver, the sampling being driven by an internal-clock of the receiver.

In some applications, receiving the power-and-data signal includes receiving the power-and-data signal by a receiver, and the method further includes synchronizing the receiver to a transmitter of the power-and-data signal by:
detecting a transition during each of the time intervals, the transition selected from the group consisting of: (i) a transition between the high-level power-and-data signal portion and the low-level power-and-data signal portion, and (ii) a transition between the low-level power-and-data signal portion and the high-level power-and-data signal portion, and verifying that a sequence of the transitions corresponds to a synchronization sequence of bits.

There is further provided, in accordance with some applications of the present invention, a method for use with a source set of consecutive digital data bits, the method including:

generating a signal in which are encoded no more data bits than are in the source set of consecutive digital data bits; and using an on-off, amplitude-modulation encoding scheme, transmitting the signal with a duty cycle that is fixed at a value of $n/(n+1)$, n being an integer greater than 1.

In some applications, n is an integer k selected from the group consisting of: 2, 3, 4, 5, 6, 7, and 8, and transmitting the signal includes transmitting the signal with a duty cycle that is fixed at $k/(k+1)$.

In some applications, n is an integer k selected from the group consisting of: 2, 3, and 4, and transmitting the signal includes transmitting the signal with a duty cycle that is fixed at $k/(k+1)$.

There is further provided, in accordance with some applications of the present invention, a method for transmission of power and data during a plurality of consecutive time intervals, the method including:

during a power-transmission portion of each of the plurality of consecutive time intervals, transmitting a power signal in which no data is encoded; and during a power-and-data-transmission portion of each of the plurality of consecutive time intervals, transmitting a power-and-data signal in which is encoded a single bit.

There is further provided, in accordance with some applications of the present invention, apparatus for transmission of power and data during a plurality of consecutive time intervals, the apparatus including a transmitter including:

a processing unit, configured to output a sequence of bits;

a modulating unit, configured to convert the sequence to an analog signal; and a light source, configured to transmit a light signal in response to the analog signal, the light signal including:

during a power-transmission portion of each of the plurality of consecutive time intervals, a power signal in which no data is encoded, and during a power-and-data-transmission portion of each of the plurality of consecutive time intervals, a power-and-data signal in which is encoded a single bit, the power-and-data signal including: (a) a high-level power-and-data signal portion, and (b) a low-level power-and-data signal portion.

In some applications:

the transmitter further includes a memory array, configured to store the sequence of bits output by the processing unit, and the modulating unit is configured to read the sequence from the memory array and convert the sequence to the analog signal.

In some applications, the apparatus is for use with a user interface, and the processing unit is configured to output the sequence of bits in response to input from the user interface.

In some applications, the apparatus is for use with a retinal prosthesis implanted in a subject, and the transmitter is configured to be mounted on eyeglasses of the subject and to transmit the power signal and the power-and-data signal toward the retinal prosthesis.

In some applications, the light source includes an infrared light source configured to transmit an infrared light signal, the infrared light signal including the power signal and the power-and-data signal.

In some applications, the infrared light source includes a transmitting element selected from the group consisting of: a light-emitting diode, and a laser.

In some applications, the modulating unit is configured to make respective durations of (a) the high-level power-and-data signal portion, and (b) the low-level power-and-data signal portion, the same as each other, during each of the plurality of consecutive time intervals.

In some applications, the modulating unit is configured to make respective transmission duty cycles, in each of at least eight consecutive ones of the plurality of consecutive time intervals, the same as each other.

In some applications, the modulating unit is configured to make respective transmission duty cycles, in each of at least four consecutive ones of the plurality of consecutive time intervals, the same as each other.

In some applications, the modulating unit is configured to make respective durations of the power-transmission portion, in each of at least eight consecutive ones of the plurality of consecutive time intervals, the same as each other.

In some applications, the modulating unit is further configured to make respective durations of the power-and-data-transmission portion, in each of the at least eight consecutive ones of the plurality of consecutive time intervals, the same as each other.

In some applications, the modulating unit is configured to make respective durations of the power-transmission portion, in each of at least four consecutive ones of the plurality of consecutive time intervals, the same as each other.

In some applications, the modulating unit is further configured to make respective durations of the power-and-data-transmission portion, in each of the at least four consecutive ones of the plurality of consecutive time intervals, the same as each other.

In some applications, the modulating unit is configured to regulate a transmission duty cycle, in each of the plurality of consecutive time intervals, independently of the data.

In some applications, the modulating unit is further configured to regulate the transmission duty cycle, in each of the plurality of consecutive time intervals, in response to a parameter that is independent of the data.

In some applications, the apparatus further includes a sensor configured to sense the parameter, and the modulating unit is configured to regulate the transmission duty cycle, in each of the plurality of consecutive time intervals, in response to the sensed parameter.

In some applications, the sensor is configured to sense a level of ambient light, and the modulating unit is configured to regulate the transmission duty cycle in response to the sensed level of ambient light.

In some applications, the sensor is configured to sense a level of ambient infrared light, and the modulating unit is configured to regulate the transmission duty cycle in response to the sensed level of ambient infrared light.

In some applications, the sensor is configured to sense a level of ambient visible light, and the modulating unit is configured to regulate the transmission duty cycle in response to the sensed level of ambient visible light.

In some applications, the modulating unit is configured to increase the transmission duty cycle in response to an increase in the sensed level of ambient light.

In some applications, the modulating unit is configured to regulate (i) a maximum amplitude of the power signal, and (ii)

a maximum amplitude of the power-and-data signal, in each of the plurality of consecutive time intervals, independently of the data.

In some applications, the modulating unit is configured to make a transmission duty cycle, in each of the plurality of consecutive time intervals, fixed at exactly one value.

In some applications, the modulating unit is configured to regulate a duty cycle of the power-and-data-signal independently of the data.

In some applications, the plurality of consecutive time intervals include at least eight consecutive time intervals, and the apparatus is configured to transmit power and data during each of the at least eight consecutive time intervals.

In some applications, the plurality of consecutive time intervals include at least four consecutive time intervals, and the apparatus is configured to transmit power and data during each of the at least four consecutive time intervals.

In some applications, the modulating unit is configured to make a transmission duty cycle, in each of the plurality of consecutive time intervals, have a value n/(n+1), n being an integer greater than one.

In some applications, the modulating unit is configured to make a transmission duty cycle, in each of the plurality of consecutive time intervals, have a value between 65% and 90%.

In some applications, the modulating unit is configured to make a transmission duty cycle, in each of the plurality of consecutive time intervals, have a value of two thirds.

In some applications, the modulating unit is configured to make a transmission duty cycle, in each of the plurality of consecutive time intervals, have a value of three fourths.

In some applications, the light signal includes an amplitude-modulated signal, and the light source is configured to transmit the amplitude-modulated signal.

In some applications, the amplitude-modulated signal includes an amplitude-shift-keyed signal, and the light source is configured to transmit the amplitude-shift-keyed signal.

In some applications, the amplitude-shift-keyed signal includes an on-off encoded signal, and the light source is configured to transmit the on-off encoded signal.

In some applications, the on-off encoded signal includes a Manchester encoded signal, and the light source is configured to transmit the Manchester encoded signal.

In some applications, for each of the plurality of consecutive time intervals, the modulating unit is configured to make a length of the power transmission portion be between 30% and 80% of a length of the time interval.

In some applications:
the power-and-data signal includes a synchronization signal, in which is encoded a bit from a synchronization sequence of bits, during at least some of the plurality of consecutive time intervals, and
the light source is configured to transmit the synchronization signal.

In some applications:
the power-and-data signal includes the synchronization signal during at least sixteen consecutive ones of the plurality of consecutive time intervals, and
the light source is configured to transmit the synchronization signal during the at least sixteen consecutive ones of the plurality of consecutive time intervals.

There is further provided, in accordance with some applications of the present invention, a method for transmitting power and data to an implanted device during a plurality of consecutive time intervals, the method including:

during each of the plurality of consecutive time intervals, transmitting a power-and-data light signal in which is encoded a single bit of data, by:
during a first sub-interval of the time interval, transmitting a first power-and-data signal portion in which a property of the transmitted light has a first value; and
during a second sub-interval of the time interval, transmitting a second power-and-data signal portion in which the property of the transmitted light has a second value that is distinct from the first value,
the property of the transmitted light being selected from the group consisting of: polarization, and wavelength;
using power from the power-and-data light signal to power the implanted device; and
using the bits of data encoded in the power-and-data light signal to control the implanted device.

In some applications, respective durations of (a) the first power-and-data signal portion, and (b) the second power-and-data signal portion, are the same as each other, during each of the plurality of consecutive time intervals.

In some applications, the method further includes configuring respective durations of the first power-and-data signal portion in each of at least eight consecutive ones of the plurality of consecutive time intervals to be the same as each other.

In some applications, the method further includes configuring respective durations of the second power-and-data signal portion in each of the at least eight consecutive ones of the plurality of consecutive time intervals to be the same as each other.

In some applications, the method further includes configuring respective durations of the first power-and-data signal portion in each of at least four consecutive ones of the plurality of consecutive time intervals to be the same as each other.

In some applications, the method further includes configuring respective durations of the second power-and-data signal portion in each of the at least four consecutive ones of the plurality of consecutive time intervals to be the same as each other.

In some applications, the method further includes configuring amplitudes of the first and second power-and-data signal portions in each of the plurality of consecutive time intervals to be dependent on a parameter that is independent of the data.

In some applications, the method further includes sensing the parameter and configuring the amplitudes in each of the plurality of consecutive time intervals to be dependent on the sensed parameter.

In some applications, sensing includes sensing a level of ambient light, and configuring the amplitudes to be dependent on the sensed parameter includes configuring the amplitudes to be dependent on the sensed level of ambient light.

In some applications, sensing the level of ambient light includes sensing a level of ambient infrared light, and configuring the amplitudes to be dependent on the sensed level of ambient light includes configuring the amplitudes to be dependent on the sensed level of ambient infrared light.

In some applications, sensing the level of ambient light includes sensing a level of ambient visible light, and configuring the amplitudes to be dependent on the sensed level of ambient light includes configuring the amplitudes to be dependent on the sensed level of ambient visible light.

In some applications, configuring the amplitudes to be dependent on the sensed level of ambient light includes configuring the amplitudes to increase in response to an increased sensed level of ambient light.

In some applications, the plurality of consecutive time intervals include at least eight consecutive time intervals, and transmitting the power-and-data light signal during each of the plurality of consecutive time intervals includes transmitting the power-and-data light signal during each of the at least eight consecutive time intervals.

In some applications, the plurality of consecutive time intervals include at least four consecutive time intervals, and transmitting the power-and-data light signal during each of the plurality of consecutive time intervals includes transmitting the power-and-data light signal during each of the at least four consecutive time intervals.

In some applications, transmitting the power-and-data light signal includes transmitting an infrared power-and-data light signal.

In some applications, transmitting the infrared power-and-data light signal includes transmitting the infrared power-and-data light signal from a transmitting element selected from the group consisting of: a light-emitting diode, and a laser.

In some applications, using the bits of data encoded in the power-and-data light signal to control the implanted device includes:
 using a filter, during each of the plurality of consecutive time intervals, filtering the power-and-data light signal to yield a data signal, by allowing passage through the filter of a single signal portion selected from the group consisting of: the first power-and-data signal portion, and the second power-and-data signal portion;
 using a data receiver, receiving the data signal; and
 controlling the implanted device in response to the data signal.

In some applications, the selected property is polarization, and using the filter to filter the power-and-data light signal includes using a polarizer.

In some applications, the selected property is wavelength, and using the filter to filter the power-and-data light signal includes using a wavelength filter.

In some applications:
 using the data receiver to receive the data signal includes using a photodiode to receive the data signal, and
 using power from the power-and-data light signal to power the implanted device includes using a photovoltaic cell to receive power from the power-and-data light signal.

In some applications, the method further includes synchronizing the data receiver to a transmitter of the power-and-data light signal by:
 detecting a transition during each of the time intervals, the transition selected from the group consisting of: (i) a transition between the selected signal portion and a low-level data signal portion, and (ii) a transition between a low-level data signal portion and the selected signal portion, and
 verifying that a sequence of the transitions corresponds to a synchronization sequence of bits.

In some applications:
 the power-and-data light signal includes a synchronization signal, in which is encoded a bit from a synchronization sequence of bits, during at least some of the plurality of consecutive time intervals, and
 transmitting the power-and-data light signal includes transmitting the synchronization signal.

In some applications:
 the power-and-data light signal includes the synchronization signal during at least sixteen consecutive ones of the plurality of consecutive time intervals, and
 transmitting the synchronization signal includes transmitting the synchronization signal during the at least sixteen consecutive ones of the plurality of consecutive time intervals.

In some applications, transmitting the power-and-data light signal during each of the plurality of consecutive time intervals includes:
 transmitting the first power-and-data signal portion by transmitting the light through an adjustable filter during the first sub-interval of the time interval; and
 transmitting the second power-and-data signal portion by transmitting the light through the adjustable filter during the second sub-interval of the time interval,
 the adjustable filter being configured to:
  during the first sub-interval, block passage therethrough of light of which the selected property has the second value, and
  during the second sub-interval, block passage therethrough of light of which the selected property has the first value.

In some applications, the selected property is polarization, and, during each of the first and second sub-intervals, transmitting the light through the adjustable filter includes transmitting the light through an adjustable polarizer.

In some applications, the selected property is wavelength, and, during each of the first and second sub-intervals, transmitting the light through the adjustable filter includes transmitting the light through an adjustable wavelength filter.

In some applications, transmitting the power-and-data light signal during each of the plurality of consecutive time intervals includes:
 using first and second transmitting elements:
  using the first transmitting element, transmitting the first power-and-data signal portion, while not transmitting with the second transmitting element; and
  using the second transmitting element, transmitting the second power-and-data signal portion, while not transmitting with the first transmitting element.

In some applications, the method further includes transmitting a power signal, in which no data is encoded, during a power-only signal period, by simultaneously (a) transmitting light from the first transmitting element, and (b) transmitting light from the second transmitting element.

There is further provided, in accordance with some applications of the present invention, apparatus for transmission of power and data during a plurality of consecutive time intervals, the apparatus including:
 a transmitter configured to transmit a power-and-data light signal, the transmitter including:
  a processing unit, configured to output a sequence of bits;
  at least one light source, configured to emit a light beam; and
  a modulating unit configured to, during each of the plurality of consecutive time intervals, encode in the light beam a single bit of the sequence of bits, by causing a property of the light beam to:
   during a first sub-interval of the time interval, have a first value, and
   during a second sub-interval of the time interval, have a second value that is distinct from the first value,
   the property being selected from the group consisting of: polarization, and wavelength.

In some applications, the apparatus further includes an adjustable filter, and the modulating unit is configured to encode in the light beam the single bit by driving the adjustable filter to:
 during the first sub-interval, block passage therethrough of light of which the property has the second value, and during the second sub-interval, block passage therethrough of light of which the property has the first value.

In some applications, the selected property is polarization, and the adjustable filter includes an adjustable polarizer.

In some applications, the selected property is wavelength, and the adjustable filter includes an adjustable wavelength filter.

In some applications, the modulating unit is configured to encode in the light beam the single bit by driving the at least one light source to:
 during the first sub-interval, emit light of which the property has the first value, and
 during the second sub-interval, emit light of which the property has the second value.

In some applications, the at least one light source includes:
 a first light source, configured to emit light of which the property has the first value; and
 a second light source, configured to emit light of which the property has the second value.

In some applications:
 the selected property is polarization,
 the first light source is configured to emit light having a first polarization, and
 the second light source is configured to emit light having a second polarization distinct from the first polarization.

In some applications:
 the selected property is wavelength,
 the first light source is configured to emit light having a first wavelength, and
 the second light source is configured to emit light having a second wavelength distinct from the first wavelength.

In some applications, the transmitter is further configured to transmit a power-only light signal, in which no data is encoded, during a power-only signal period, by:
 the light beam including light emitted simultaneously from the first and second light sources, and
 the modulating unit being configured to not encode any data in the light beam.

In some applications:
 the transmitter further includes a memory array, configured to store the sequence of bits output by the processing unit, and
 the modulating unit is configured to read the sequence from the memory array.

In some applications, the apparatus is for use with a user interface, and the processing unit is configured to output the sequence of bits in response to input from the user interface.

In some applications, the apparatus is for use with a retinal prosthesis implanted in a subject, and the transmitter is configured to be mounted on eyeglasses of the subject and to transmit the power-and-data light signal toward the retinal prosthesis.

In some applications, the light beam includes an infrared light beam, and the at least one light source includes at least one infrared light source configured to transmit the infrared light beam.

In some applications, the at least one infrared light source includes a transmitting element selected from the group consisting of: a light-emitting diode, and a laser.

In some applications, the modulating unit is configured to make respective durations of (a) the first sub-interval, and (b) the second sub-interval, the same as each other, during each of the plurality of consecutive time intervals.

In some applications, the modulating unit is configured to make respective durations of the first sub-interval, in each of at least eight consecutive ones of the plurality of consecutive time intervals, the same as each other.

In some applications, the modulating unit is further configured to make respective durations of the second sub-interval, in each of the at least eight consecutive ones of the plurality of consecutive time intervals, the same as each other.

In some applications, the modulating unit is configured to make respective durations of the first sub-interval, in each of at least four consecutive ones of the plurality of consecutive time intervals, the same as each other.

In some applications, the modulating unit is further configured to make respective durations of the second sub-interval, in each of the at least four consecutive ones of the plurality of consecutive time intervals, the same as each other.

In some applications, the plurality of consecutive time intervals include at least eight consecutive time intervals, and the apparatus is configured to transmit power and data during each of the at least eight consecutive time intervals.

In some applications, the plurality of consecutive time intervals include at least four consecutive time intervals, and the apparatus is configured to transmit power and data during each of the at least four consecutive time intervals.

There is further provided, in accordance with some applications of the present invention, apparatus for receiving a power-and-data light signal during a plurality of consecutive time intervals, wherein, during each of the plurality of consecutive time intervals, (a) the power-and-data light signal includes (i) a first power-and-data signal portion, and (ii) a second power-and-data signal portion, and (b) a single bit of data is encoded in the power-and-data light signal,
 the apparatus including:
 a receiving unit, including:
 a power receiver, configured to receive power by receiving the power-and-data light signal;
 a data receiver structurally distinct from the power receiver; and
 a filter, configured to allow passage to the data receiver of a single signal portion selected from the group consisting of: the first power-and-data signal portion, and the second power-and-data signal portion,
 the data receiver being configured to receive the data by receiving the selected signal portion.

In some applications, the filter includes a polarizer.

In some applications, the filter includes a wavelength filter.

In some applications, the apparatus includes an implanted device that includes the receiving unit, the implanted device being configured to:
 be powered by power received by the power receiver, and
 be controlled by the data received by the data receiver.

In some applications, the implanted device includes a retinal prosthesis.

There is further provided, in accordance with some applications of the present invention, a method for receiving a power-and-data light signal during a plurality of consecutive time intervals, wherein, during each of the plurality of consecutive time intervals, (a) the power-and-data light signal includes (i) a first power-and-data signal portion, and (ii) a second power-and-data signal portion, and (b) a single bit of data is encoded in the power-and-data light signal,
 the method including:
 using a receiving unit that includes a power receiver, a data receiver, and a filter:
 using the power receiver, receiving power by receiving the power-and-data light signal;
 using the filter, allowing passage to the data receiver of a single signal portion selected from the group consisting of: the first power-and-data signal portion, and the second power-and-data signal portion; and using the data receiver, receiving the data by receiving the selected signal portion.

In some applications, using the filter includes using a polarizer.

In some applications, using the filter includes using a wavelength filter.

In some applications, the method further includes:

powering an implanted device using the received power, the implanted device including the receiving unit; and controlling the implanted device using the received data.

In some applications:

the implanted device includes a retinal prosthesis, and powering the implanted device includes powering the retinal prosthesis.

The present invention will be more fully understood from the following detailed description of embodiments thereof, taken together with the drawings, in which:

BRIEF DESCRIPTION OF THE DRAWINGS

FIGS. 6A-B are schematic illustrations of two signals transmitting power and data during a plurality of consecutive time intervals, in accordance with some applications of the present invention;

FIG. 10 is a schematic illustration of a method for transmission of power and data during a plurality of consecutive time intervals, in accordance with some applications of the present invention;

FIGS. 11A-B and FIGS. 12-13 are schematic illustrations of a method for receiving power and data during a plurality of consecutive time intervals, in accordance with some applications of the present invention;

FIG. 16 is a schematic illustration of a method for transmission of power and data during a plurality of consecutive time intervals, in accordance with some applications of the present invention;

FIGS. 17A-B are schematic illustrations of a signal transferring power and data, in accordance with some applications of the present invention;

FIG. 18 is a schematic illustration of a method for transmitting power and data to an implanted device during a plurality of consecutive time intervals, in accordance with some applications of the present invention;

FIG. 20 is a schematic illustration of a data signal, in accordance with some applications of the present invention; and FIGS. 21A-B are schematic illustrations of apparatus for transmission of power and data during a plurality of consecutive time intervals, in accordance with some applications of the present invention.

DETAILED DESCRIPTION OF EMBODIMENTS

Figure 1:
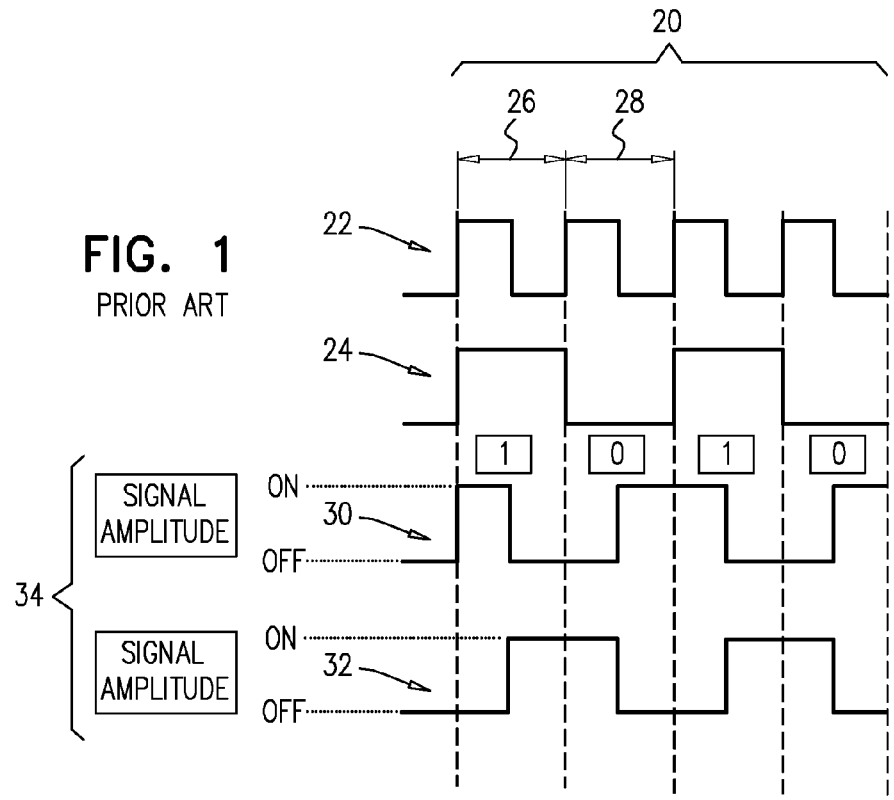
FIG. 1 is a schematic illustration of a prior-art method for transmission of data during a plurality of consecutive time intervals, in accordance with some applications of the present invention.

Reference is made to FIG. 1, which is a schematic illustration of a prior-art method for transmission of data during a plurality 20 of consecutive time intervals. (Four such intervals are shown in FIG. 1, the intervals being separated by vertical dashed lines.) Specifically, FIG. 1 shows two versions 30 and 32 of the Manchester encoding scheme 34. During each of time intervals 20, a clock signal 22 regulates the encoding of a single bit from a sequence 24 of data bits. Each bit is encoded by a high-to-low or low-to-high transition coinciding with the transition of clock signal 22 at the middle of the time interval. For example, during time interval 26, a "1" from sequence 24 is encoded by a high-to-low transition (version 30) or a low-to-high transition (version 32). Conversely, during time interval 28, a "0" from sequence 24 is encoded by a low-to-high transition (version 30) or a high-to-low transition (version 32). As shown in FIG. 1, encoding scheme 34 is a type of on-off keying encoding scheme, whereby the signal that encodes the data is either "on" at some constant (and typically maximal) amplitude, or "off", which typically means it has zero amplitude. On-off keying is a form of amplitude-shift keying (ASK), which in turn is a form of amplitude modulation.

If a data-encoding signal is to be used also to transmit power, a relevant parameter of the signal—and hence, of the encoding scheme used to generate the signal—is the duty cycle. The duty cycle expresses the power transmitted during a given time period as a percentage of the maximum amount of power that can be transmitted during the time period. As can be seen from FIG. 1, the duty cycle of Manchester encoding scheme 34 has a fixed, i.e., data-independent, duty cycle of 50%.

Figure 2A:
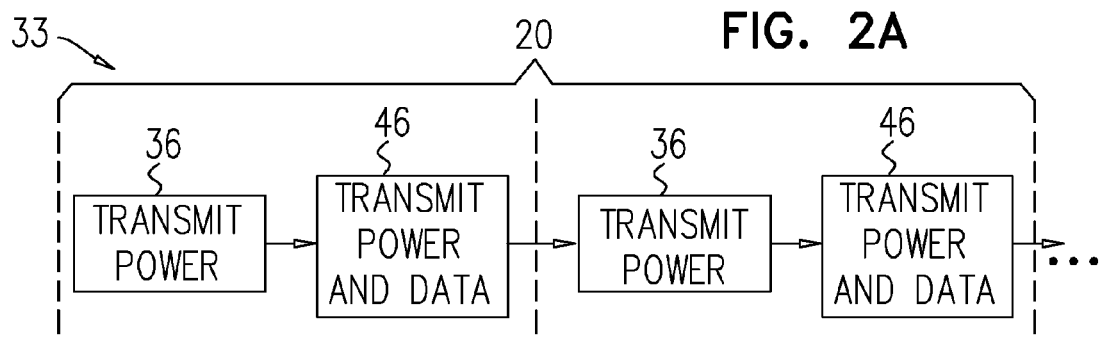
FIGS. 2A-B are flow charts of a method for transmission of power and data during a plurality of consecutive time intervals, in accordance with some applications of the present invention.
Figure 2B:
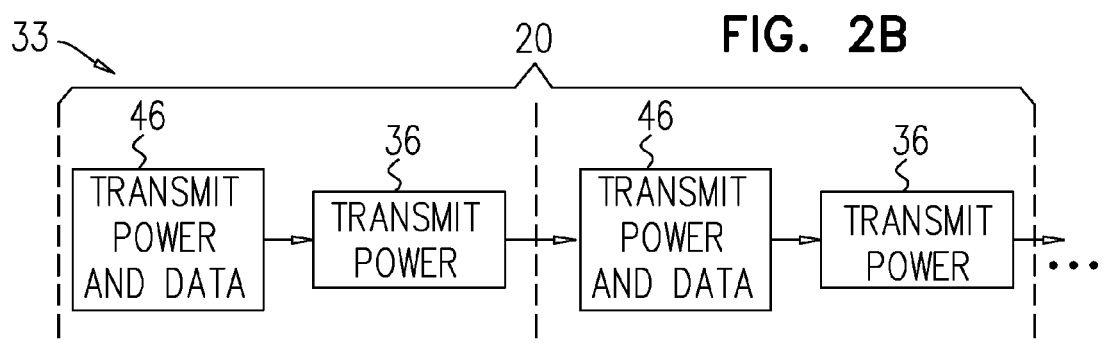

Reference is now made to FIGS. 2A-B, which are flow charts of a method 33 for transmission of power and data during a plurality 20 of consecutive time intervals, in accordance with some applications of the present invention. (Two such intervals are shown in FIGS. 2A-B, the intervals being separated by vertical dashed lines.) During a power-transmission portion 36 of each of intervals 20, a power signal, in which no data is encoded, is transmitted. During a power-and-data-transmission portion 46 of each of intervals 20, a power-and-data signal, in which is encoded a single bit, is transmitted. As described hereinbelow with reference to FIGS. 4A-B, the power-and-data signal includes: (a) a high-level power-and-data signal portion, and (b) a low-level power-and-data signal portion. In some applications, as shown in FIG. 2A, power-transmission portion 36 precedes power-and-data-transmission portion 46 during each of intervals 20. In other applications, as shown in FIG. 2B, power-and-data-transmission portion 46 precedes power-transmission portion 36. In some applications, power-transmission portion 36 includes a first portion that precedes power-and-data-transmission portion 46 and a second portion that follows power-and-data-transmission portion 46.

With respect to devices such as those described in the Background, the prior-art method of FIG. 1 is generally suboptimal, in that a duty cycle of only 50% may not provide for sufficient power transfer. As described more fully hereinbelow, method 33 generally improves upon the prior-art method of FIG. 1, in that the transmission of power during power-transmission portion 36 facilitates duty cycles greater than 50%.

Figure 3:
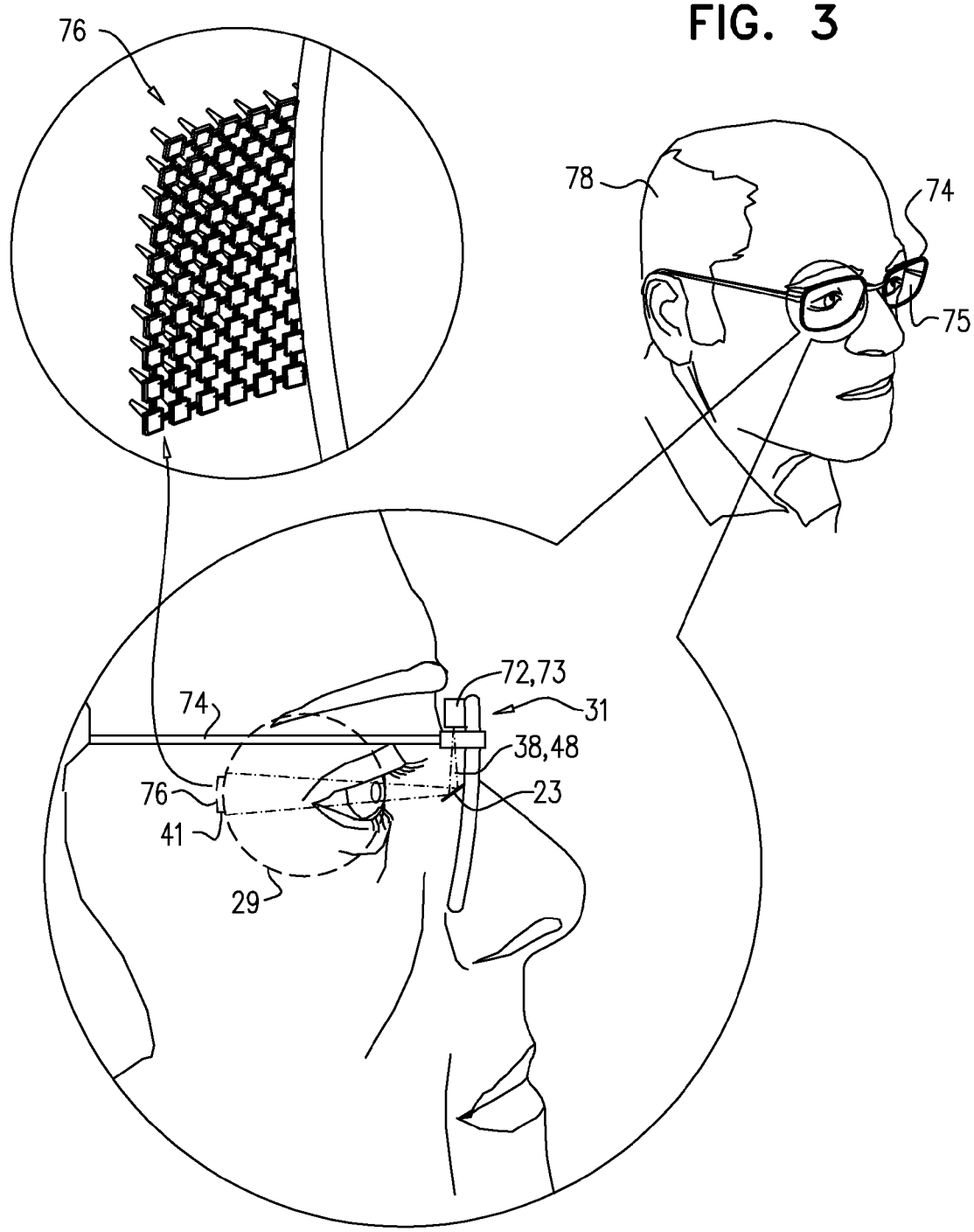
FIG. 3 is a schematic illustration of apparatus for transmission of power and data, in accordance with some applications of the present invention.
Figure 4A:
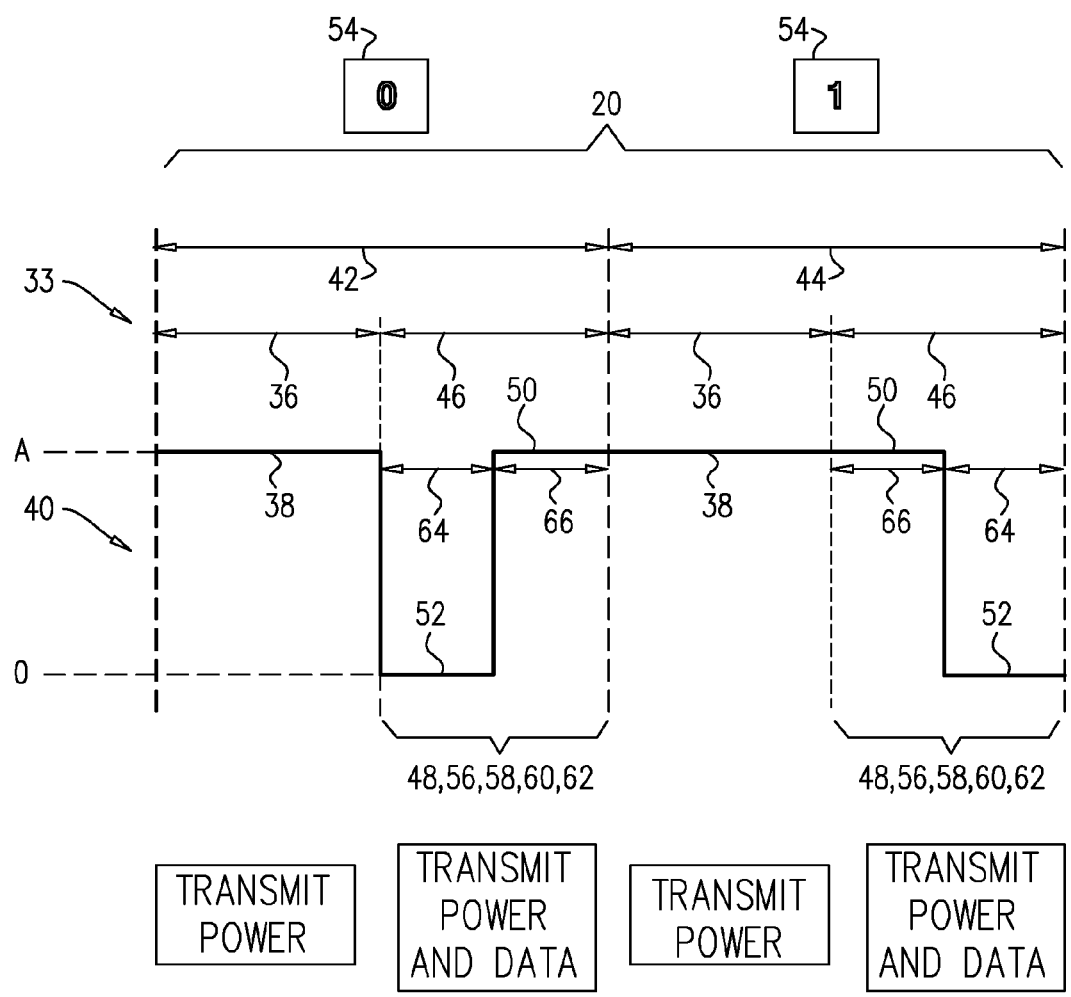
FIGS. 4A-B and FIG. 5 are schematic illustrations of a method for transmission of power and data during a plurality of consecutive time intervals, in accordance with some applications of the present invention.
Figure 4B:
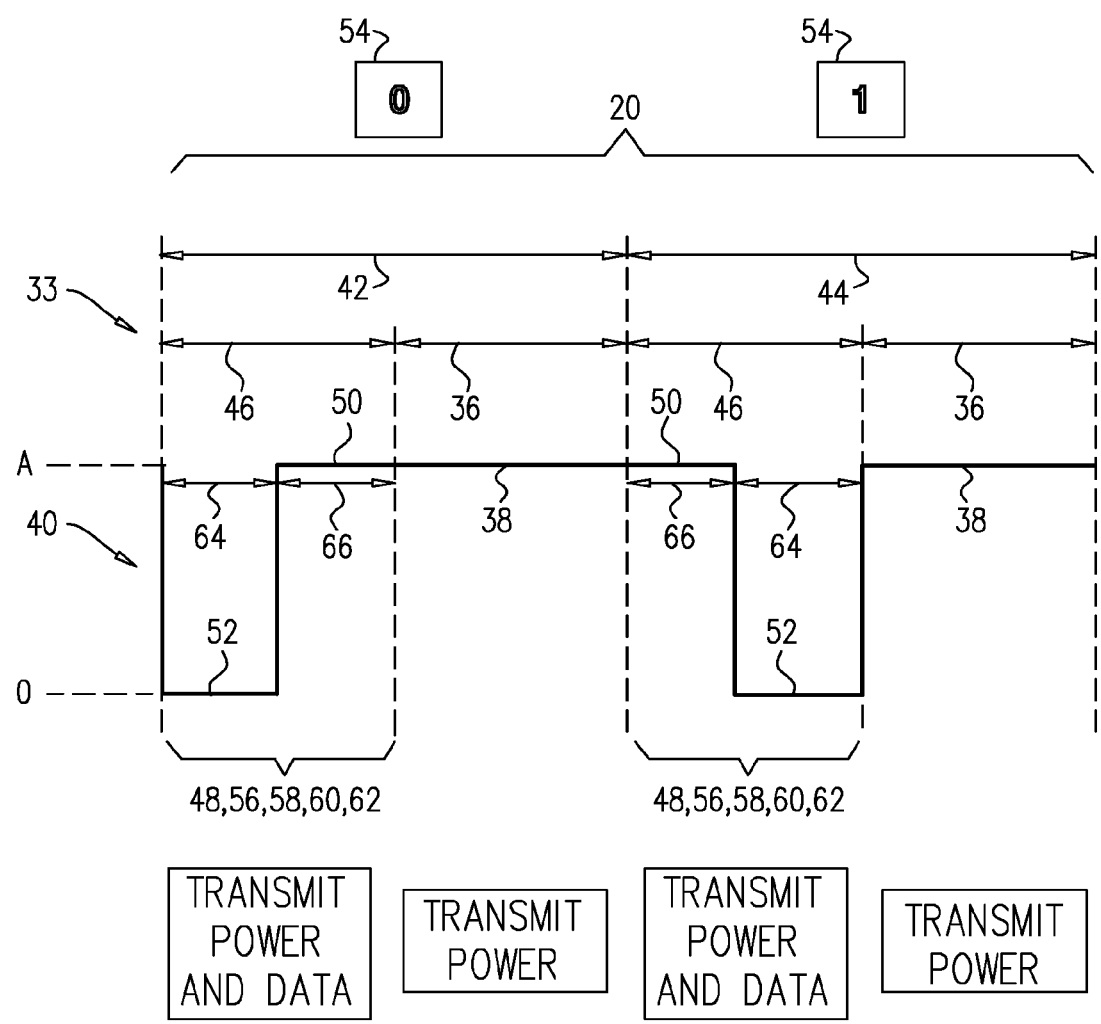

Reference is now made to FIG. 3, which is a schematic illustration of apparatus 31 for transmission of power and data, in accordance with some applications of the present invention. Reference is also made to FIGS. 4A-B, which are schematic illustrations of method 33 for transmission of power and data during a plurality 20 of consecutive time intervals, in accordance with some applications of the present invention. (FIGS. 4A-B show method 33 of FIGS. 2A-B in more detail; FIG. 4A corresponds to FIG. 2A, while FIG. 4B corresponds to FIG. 2B.)

Apparatus 31 comprises a transmitter 72, configured to transmit power and data in accordance with method 33. Specifically, transmitter 72 is configured to transmit a power signal 38, in which no data is encoded, during a power-transmission portion 36 of each of intervals 20, and to transmit a power-and-data signal 48, in which is encoded a single bit, during a power-and-data-transmission portion 46 of each of intervals 20. Power-and-data signal 48 includes: (a) a high-level power-and-data signal portion 50, and (b) a low-level power-and-data signal portion 52.

As shown in FIG. 3, in some applications, apparatus 31 is for use with a retinal prosthesis 76 implanted in the retina 41 of an eye 29 of a subject 78. In these applications, transmitter 72 is typically mounted on eyeglasses 74 of subject 78, and transmits signals 38 and 48 toward prosthesis 76. By way of example, FIG. 3 shows signals 38 and 48 directed toward prosthesis 76 via reflection off of a mirror 23.

FIGS. 4A-B show a signal 40 used to transmit both power and data during a plurality 20 of time intervals, in accordance with method 33 as illustrated in FIGS. 2A-B. (Two such time intervals are shown, separated by a thick dashed line.) During power-transmission portion 36 of each of time intervals 20, a power signal 38, in which no data is encoded, is transmitted. During power-transmission portion 36, signal 40 is always on, and is typically at a maximum amplitude A so as to maximize transfer of power. In some applications, as shown in FIG. 4A, power-transmission portion 36 precedes power-and-data-transmission portion 46 during each of intervals 20. In other applications, as shown in FIG. 4B, power-and-data-transmission portion 46 precedes power-transmission portion 36. In some applications, power-transmission portion 36 includes a first portion that precedes power-and-data-transmission portion 46 and a second portion that follows power-and-data-transmission portion 46. During power-and-data-transmission portion 46 of each of intervals 20, a power-and-data signal 48 is transmitted. A single bit 54 is encoded in power-and-data signal 48 during each of intervals 20. Power-and-data signal 48 includes (a) a high-level power-and-data signal portion 50, and (b) a low-level power-and-data signal portion 52. Typically, as shown in FIGS. 4A-B, transmitting power-and-data signal 48 comprises transmitting an amplitude-modulated signal 56, in which information is encoded by variations in amplitude of signal 48. Further typically, transmitting amplitude-modulated signal 56 comprises transmitting an amplitude-shift-keyed signal 58, in which bit 54 is encoded by variations in amplitude of signal 48. In some applications, transmitting amplitude-shift-keyed signal comprises transmitting an on-off encoded signal 60, which assumes either an "on" or "off" state. When on, signal 60 is typically at maximum amplitude A. When off, signal 60 typically has an amplitude of zero.

In some applications, transmitting on-off encoded signal 60 comprises transmitting a Manchester encoded signal 62. (As noted above, method 33 differs from the prior art, despite the utilization of encoding scheme 34, at least in that signal 40 additionally includes a power signal 38 during each of intervals 20.) Manchester encoded signal 62 uses encoding scheme 34, described with reference to FIG. 1, to encode bits 54. FIGS. 4A-B show the utilization of version 30 of scheme 34 (FIG. 1). Thus, the first bit 54, which is a zero, is encoded by a low-to-high transition midway through power-and-data-transmission portion 46 of the first time interval 42, while the second bit 54, which is a one, is encoded by a high-to-low transition midway through power-and-data-transmission portion 46 of the second time interval 44.

Although the figures in the present application generally show the utilization of version 30 of scheme 34, the scope of the present invention also allows for the utilization of version 32 of scheme 34.

Typically, the duration 66 of the high-level power-and-data signal portion 50 is the same as the duration 64 of the low-level power-and-data signal portion 52, during each of the plurality of consecutive time intervals 20. For example, in some applications, as described above, Manchester encoded signal 62 is transmitted during power-and-data-transmission portion 46. In these applications, the high-to-low or low-to-high transition is midway through power-and-data-transmission portion 46, and thus, durations 64 and 66 are the same as each other.

The scope of the present invention allows for transmitting only power signal 38, without power-and-data signal 48, during one or more time intervals that precede or follow intervals 20. For example, if there is no need to transfer data for a period of time, applications of the present invention may transmit only power signal 38.

Figure 5:
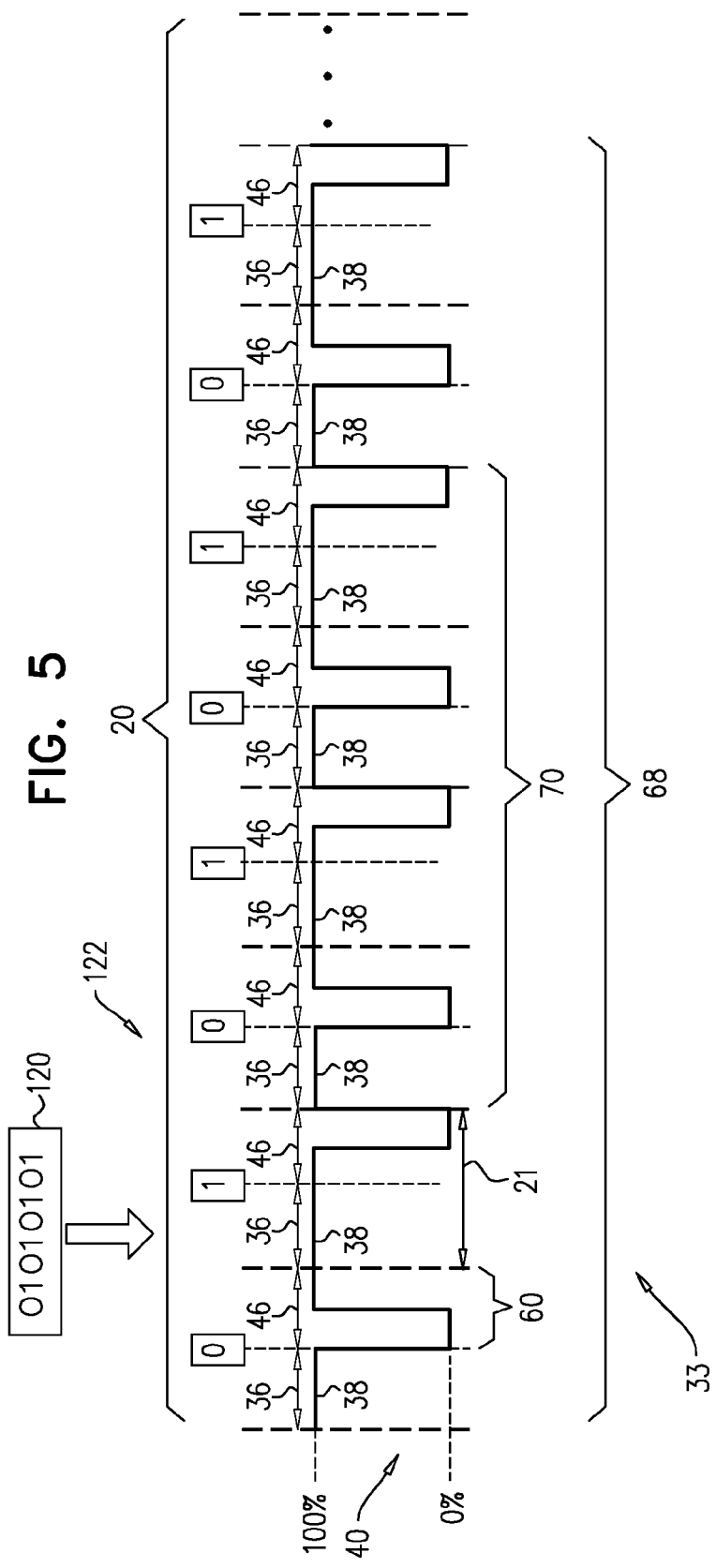

Reference is now made to FIG. 5, which is a schematic illustration of method 33 for transmission of power and data during a plurality 20 of consecutive time intervals, in accordance with some applications of the present invention. In some applications, plurality 20 of consecutive time intervals includes at least four consecutive time intervals 70. During power-transmission portions 36 of intervals 70, power signal 38 is transmitted. In some applications, plurality 20 of consecutive time intervals includes at least eight consecutive time intervals 68. During power-transmission portions 36 of intervals 68, power signal 38 is transmitted.

The transmission duty cycle of a particular one of time intervals 20 may be calculated by dividing the power transmitted during the time interval by the maximum amount of power that can be transmitted during the interval. In the example shown in FIG. 5, for each of time intervals 20 shown, signal 40 transmits power at 100% for all of power-transmission portion 36, and for half of power-and-data-transmission portion 46. For the other half of power-and-data-transmission portion 46, signal 40 transmits power at 0%. Hence, the transmission duty cycle is 75%, or three fourths.

Typically, the respective transmission duty cycles in each of the at least four consecutive ones 70 of intervals 20 are configured to be the same as each other. Further typically, the respective transmission duty cycles in each of the at least eight consecutive ones 68 of intervals 20 are configured to be the same as each other.

Typically, the respective durations of power transmission portion 36 in each of the at least four consecutive ones 70 of intervals 20 are configured to be the same as each other. Typically, the respective durations of power transmission portion 36 in each of the at least eight consecutive ones 68 of intervals 20 are configured to be the same as each other.

In some applications, the respective durations of power-and-data-transmission portion 46 in each of the at least four consecutive ones 70 of intervals 20 are configured to be the same as each other. In some applications, the respective durations of power-and-data-transmission portion 46 in each of the at least eight consecutive ones 68 of intervals 20 are configured to be the same as each other.

Reference is now made to FIGS. 6A-B, which are schematic illustrations of two signals 40a and 40b transmitting power and data during a plurality of consecutive time intervals 20, in accordance with some applications of the present invention. Typically, the transmission duty cycle in each of time intervals 20 is configured to be independent of the data. In the example shown in FIG. 6A, signal 40a encodes the bit sequence "010101". The transmission duty cycle of signal 40a in each of time intervals 20 is 75%, as explained above with respect to FIG. 5. Although signal 40b encodes a different bit sequence—namely, "000000"—it, too, has a transmission duty cycle of 75% in each of time intervals 20. (Similarly, a different bit sequence, "111111" (not shown), would also have a transmission duty cycle of 75% in each of time intervals 20.) Configuring the transmission duty cycle to be independent of the data helps maintain a steady and predictable supply of power to the device that is receiving the power-and-data signal.

Typically, power-and-data signal 48 is transmitted with a duty cycle that is independent of the data. For example, in both signals 40a and 40b, the duty cycle of power-and-data signal 48 is 50%. Configuring the duty cycle of power-and-data signal 48 to be independent of the data helps maintain a steady and predictable supply of power to the device that is receiving the power-and-data signal.

Reference is now made to FIGS. 17A-B, which are schematic illustrations of a signal 40 transferring power and data, in accordance with some applications of the present invention. In some applications, the transmission duty cycle in each of time intervals 20 is dependent on a parameter that is independent of the data. In some applications, the parameter is sensed, and the transmission duty cycle in each of the plurality of consecutive time intervals is dependent on the sensed parameter. For example, in some applications, the transmission duty cycle is dependent on a sensed level of ambient light, such as a sensed level of ambient IR light and/or a sensed level of ambient visible light. In these applications, the transmission duty cycle is typically inversely related to the sensed level of ambient light. For example, an increase in ambient light typically increases noise that interferes with the transfer of data, such that for some applications, it is desirable to have the duty cycle decrease in response to an increase in ambient light. FIG. 17A shows the duty cycle being decreased in response to an increase in ambient light. Initially, portions 36 and 46 of time interval 42 have the same duration, and the duty cycle is ¾. Following an increase in ambient light, power-and-data-transmission portion 46 is lengthened, while power transmission portion 36 is shortened, such that the new duty cycle is ⅔. (The length of time interval 42 remains constant.) The lengthening of power-and-data-transmission portion 46 helps increase the signal-to-noise ratio (SNR), such as to at least partially compensate for noise added by the increase in ambient light.

In some applications, the transmission duty cycle is alternatively or additionally dependent on other factors. For example, in some applications, prosthesis 76 provides feedback to transmitter 72 (FIG. 3), the feedback containing data used for checking transmission fidelity, e.g., a checksum, and/or data pertaining to a level of received power. The transmission duty cycle is regulated in response to the feedback; for example, if transmission fidelity is low, the transmission duty cycle may be lowered via lengthening of power-and-data-transmission portion 46.

In some applications, the amplitudes of power signal 38 and power-and-data signal 48 are also dependent on the sensed parameter. For example, FIG. 17B shows a scenario in which, as described above with respect to FIG. 17A, power-and-data-transmission portion 46 has been lengthened, and power transmission portion 36 shortened, in response to an increase in ambient light. As described above, the lengthening of portion 46 helps increase the SNR; however, the resultant duty cycle of ⅔ may not provide for sufficient power transfer, assuming no change in the amplitudes of the signals. Therefore, the maximum amplitudes of the signals are increased from A to B, in order to provide for sufficient power transfer.

In some applications, the transmission duty cycle in each of time intervals 20 is fixed at exactly one value. In these applications, the transmission duty cycle does not automatically change in response to changes in sensed parameters, such as the level of ambient light, and the transmission duty cycle is typically not a variable that can be controlled under normal operation of the apparatus.

Reference is again made to FIG. 3. In some applications, lenses 75 of the subject's glasses 74 (FIG. 3) are photochromic, such that they darken or lighten in response to a change in ambient light. In some applications, the use of photochromic lenses may reduce the need to change the transmission duty cycle in response to a change in ambient light, as described with respect to FIGS. 17A-B. For example, if lenses 75 darken in response to an increase in ambient light, the transmission duty cycle may remain unchanged, or alternatively, may be decreased to a lesser extent, relative to if lenses 75 were not darkened.

In some applications, as described above with reference to FIG. 5, the transmission duty cycle is configured to be three fourths in each of plurality 20 of consecutive time intervals.

Figure 7:
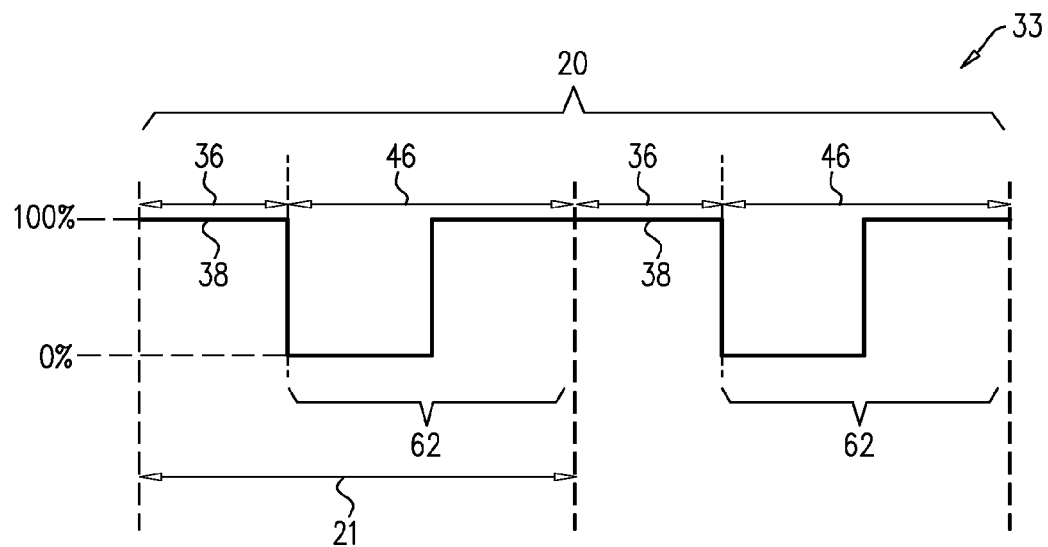
FIG. 7 is a schematic illustration of a method for transmission of power and data during a plurality of consecutive time intervals, in accordance with some applications of the present invention.

Reference is now made to FIG. 7, which is a schematic illustration of method 33 for transmission of power and data during a plurality 20 of consecutive time intervals, in accordance with some applications of the present invention. In some applications, the transmission duty cycle is configured to be two thirds in each of plurality 20 of consecutive time intervals. For example, this may be done by (a) configuring power-and-data-transmission portion 46 to be twice as long as power-transmission portion 36, and (b) transmitting a Manchester encoded signal 62 (with a duty cycle of 50%) during power-and-data-transmission portion 46, as shown in FIG. 5.

Typically, the transmission duty cycle in each of intervals 20 is configured to be $n/(n+1)$, n being an integer greater than one. (In this context, a transmission duty cycle of ½, wherein $n=1$, is the transmission duty cycle of the prior-art traditional Manchester code.) For example, applications in which $n=2$ and $n=3$ have already been shown in FIGS. 7 and 5, respectively. In some applications, the transmission duty cycle in each of intervals 20 is configured to be between 65% and 90%. For example, duty cycles of ⅔ and ¾ have already been described with reference to FIGS. 7 and 5, respectively.

Typically, for each of intervals 20, the length of power transmission portion 36, during which power signal 38 is transmitted, is between 30% and 80% of the length of the interval. For example, FIG. 5 shows the length of power transmission portion 36 being ½ of the length of time interval 21, while FIG. 7 shows the length of power transmission portion 36 being ⅓ of the length of time interval 21.

Reference is again made to FIG. 3. Typically, both power signal 38 and power-and-data signal 48 are transmitted wirelessly. For example, FIG. 3 shows transmitter 72 wirelessly transmitting signals 38 and 48 to prosthesis 76. Typically, signals 38 and 48 are transmitted using infrared transmission, so as not to disturb subject 78 or interfere with the functioning of prosthesis 76. Further typically, a single infrared transmitter 73 wirelessly transmits both power signal 38 and power-and-data signal 48.

Figure 8A:
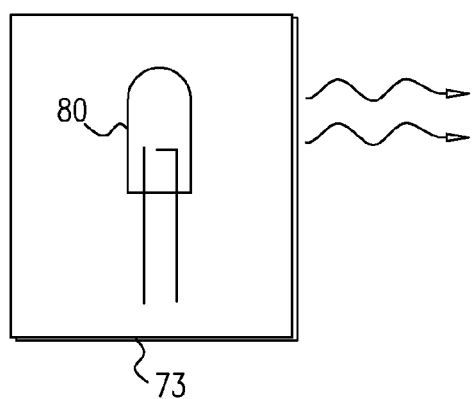
FIGS. 8A-B are schematic illustrations of transmitting elements, in accordance with some applications of the present invention.
Figure 8B:
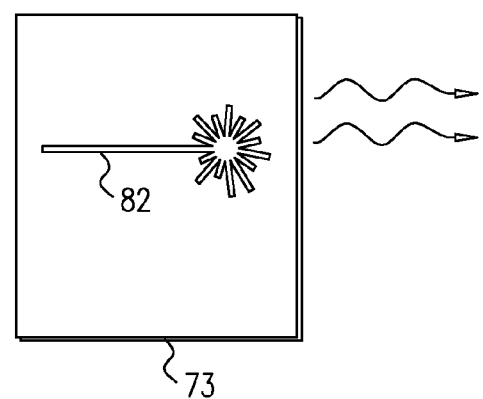

Reference is now made to FIGS. 8A-B, which are schematic illustrations of transmitting elements 80 and 82, in accordance with some applications of the present invention. Typically, transmitting signals 38 and 48 from infrared transmitter 73 comprises transmitting the signals from a light-emitting diode 80 and/or a laser 82.

Figure 9:
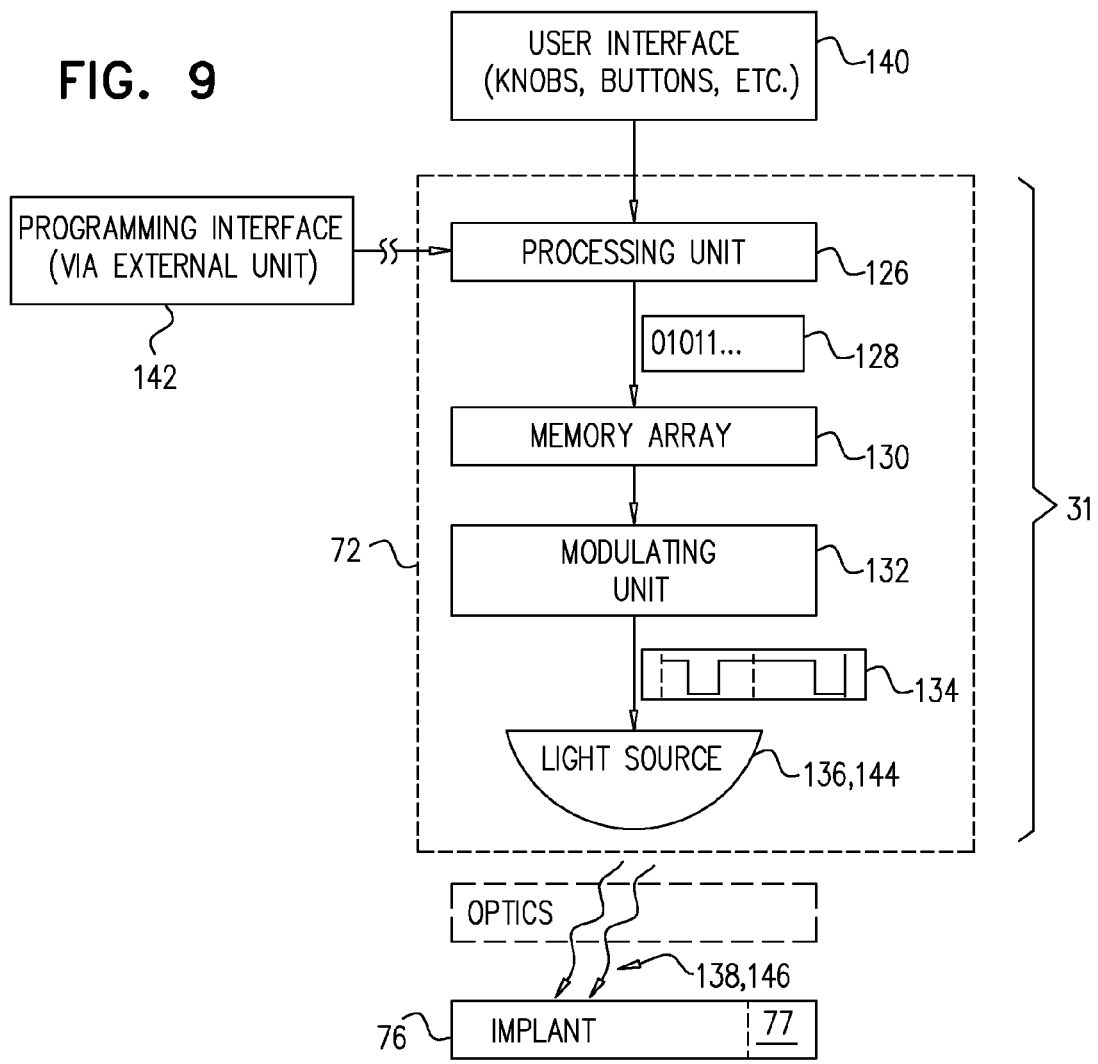
FIG. 9 is a schematic illustration of apparatus for transmission of power and data, in accordance with some applications of the present invention.

Reference is now made to FIG. 9, which is a schematic illustration of apparatus 31 for transmission of power and data, in accordance with some applications of the present invention, and to FIGS. 4A-B. FIG. 9 shows apparatus 31, described briefly above with reference to FIG. 3, in more detail. Apparatus 31 comprises transmitter 72, which comprises: (i) a processing unit 126, configured to output a sequence 128 of bits; (ii) a modulating unit 132, configured to convert the sequence to an analog signal 134; and (iii) a light source 136, configured to transmit a light signal 138 in response to the analog signal. In some applications, as shown in FIG. 9, transmitter 72 further comprises a memory array 130, configured to store sequence 128, and modulating unit 132 is configured to read the sequence from memory array 130 and convert the sequence to analog signal 134.

Transmitter 72 is configured to transmit power and data during time intervals 20 via the transmission of light signal 138. Light signal 138 is an instance of signal 40, described above with reference to FIGS. 4A-B. Accordingly, light signal 138 includes: (i) during power-transmission portion 36 of each of intervals 20, power signal 38 in which no data is encoded, and (ii) during power-and-data-transmission portion 46 of each of intervals 20, power-and-data signal 48 in which is encoded a single bit 54. Power-and-data signal 48 includes: (a) high-level power-and-data signal portion 50, and (b) low-level power-and-data signal portion 52. Light signal 138 is received by a receiver 77, located, for example, in retinal prosthesis 76. Typically, receiver 77 comprises a photovoltaic cell for receiving power, and a photodiode for receiving data.

In some applications, apparatus 31 is for use with a user interface 140. For example, apparatus 31 may comprise user interface 140. Processing unit 126 is configured to output sequence 128 of bits in response to input from user interface 140. For example, in some applications, as described above with respect to FIG. 3 and as shown schematically in FIG. 9, apparatus 31 is for use with a retinal prosthesis 76 implanted in a subject 78. In these applications, subject 78 may periodically change certain settings, e.g., a desired contrast or brightness level, via user interface 140. The change of settings is communicated to processing unit 126, which outputs sequence 128 of bits in response to the change of settings. Typically, the output of sequence 128 is controlled by instructions stored in programming interface 142.

In some applications, light source 136 comprises an infrared light source 144 configured to transmit an infrared light signal 146, the infrared light signal including power signal 38 and power-and-data signal 48. In some applications, infrared light source 146 comprises a transmitting element selected from the group consisting of: light-emitting diode 80, and laser 82 (FIGS. 8A-B).

Reference is made to FIG. 10, which is a schematic illustration of method 33 for transmission of power and data during a plurality 20 of consecutive time intervals, in accordance with some applications of the present invention. In some applications, power-and-data signal 48 includes a synchronization signal 84, in which is encoded a bit 54 from a synchronization sequence 86 of bits, during at least some intervals 88 of the plurality of consecutive time intervals 20. Transmitting power-and-data signal 48 correspondingly comprises transmitting synchronization signal 84. Sequence 86 typically consists of a fixed pattern of zeros and/or ones, such as the alternating pattern shown in FIG. 10, that is known in advance by receiver 77 (FIG. 9). Typically, sequence 86 is transmitted at the beginning of each data sequence. If receiver 77 does not identify sequence 86 at the beginning of a data sequence, receiver 77 determines that it is out of synch with transmitter (FIG. 9); for example, instead of decoding the data by sampling signal 40 before and after times 90, receiver 77 might be sampling signal 40 before and after times 91 during at least some of intervals 20. In this scenario, receiver 77 is configured to stop receiving data and/or to reject previously-received data, and to re-synchronize with transmitter 72. Receiver 77 typically "expects" sequence 86 immediately after a period of time with no data transfer, and/or after a predetermined number of bits has been received. For example, data may be transferred in packets of a fixed number of bits M, such that each packet begins with sequence 86. In this scenario, receiver 77 "expects" sequence 86 immediately following each packet of M bits.

Receiver 77 typically resynchronizes with transmitter 72 by receiving power-and-data signal 48 during each of time intervals 88 and detecting the transitions between high-level power-and-data signal portion 50 and low-level power-and-data signal portion 52, or between low-level power-and-data signal portion and high-level power-and-data signal portion 50. By verifying that the sequence of transitions during intervals 88 corresponds to synchronization sequence 86, receiver 77 determines that it is once again in synch with transmitter 72.

FIG. 10 shows N consecutive ones of intervals 20 during which power-and-data signal 48 includes synchronization signal 84. N is typically at least 4 and/or less than 20. For example, in some applications, power-and-data signal 48 includes synchronization signal 84 during at least sixteen consecutive ones of intervals 20.

FIG. 10 also shows a method 35 for transmission of power and synchronization-data during a plurality 94 of consecutive time intervals. During power-transmission portion 36 of each of intervals 94, power signal 38, in which no data is encoded, is transmitted. During a power-and-synchronization-data-transmission portion 96 of each of intervals 94, a power-and-synchronization-data signal 98 is transmitted. Power-and-synchronization-data signal 98 encodes a single bit 54 from a synchronization sequence 86 of bits, and includes (a) a high-level power-and-synchronization-data signal portion 100, and (b) a low-level power-and-synchronization-data signal portion 102. Method 35 may be practiced in combination with any of the apparatus and/or methods described above with reference to FIGS. 2-9.

Figure 11A:
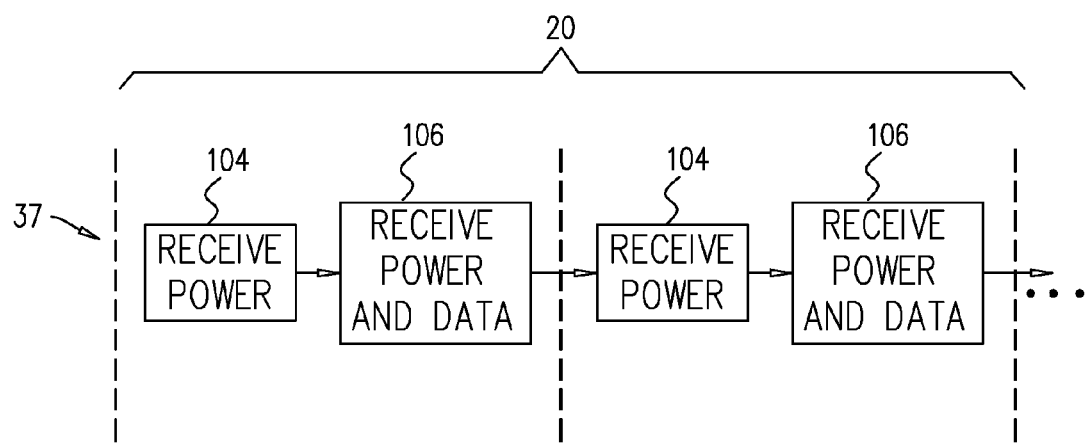
Figure 11B:
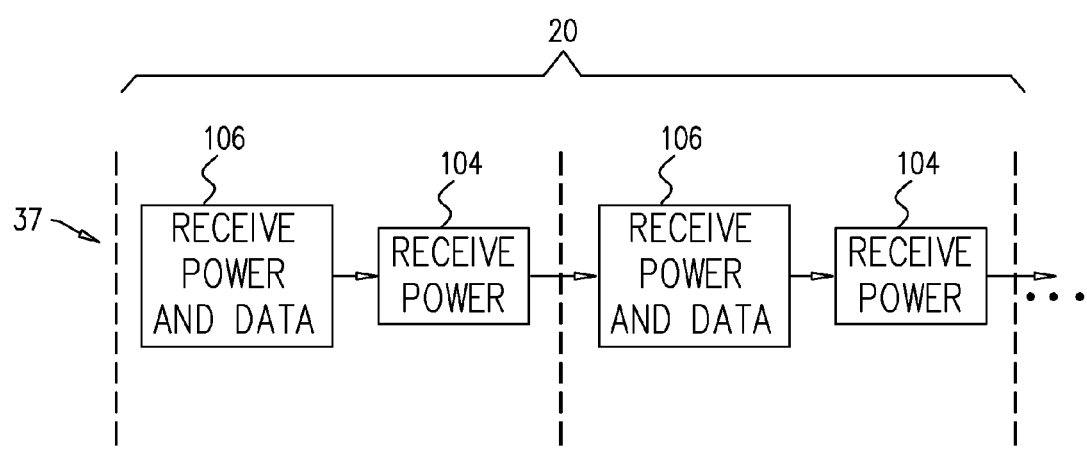

Reference is now made to FIGS. 11A-B and FIG. 12, which are schematic illustrations of a method 37 for receiving power and data during a plurality 20 of consecutive time intervals, in accordance with some applications of the present invention. During a power-receiving portion 104 of each of intervals 20, a power signal 38, in which no data is encoded, is received. During a power-and-data-receiving portion 106 of each of intervals 20, a power-and-data signal 48, in which is encoded a single bit 54, is received. As described above with respect to FIGS. 4A-B, power-and-data signal 48 includes (a) a high-level power-and-data signal portion 50, and (b) a low-level power-and-data signal portion 52.

In some applications, as shown in FIG. 11A and FIG. 12, power-receiving portion 104 precedes power-and-data-receiving portion 106 during each of intervals 20. In other applications, as shown in FIG. 11B, power-and-data-receiving portion 106 precedes power-receiving portion 104. In some applications, power-receiving portion 104 includes a first portion that precedes power-and-data-receiving portion 106 and a second portion that follows power-and-data-receiving portion 106.

In some applications, receiving power-and-data signal 48 comprises sampling power-and-data signal 48 exactly N times during each of intervals 20, and receiving power signal 38 comprises sampling power signal 38 exactly N times, N being an even integer greater than one. For example, FIG. 9 shows an application in which each of signals 48 and 38 is sampled twice, i.e., N=2. Samples 110 of signal 48 are typically used to decode the encoded data in signal 48. For example, during power-and-data-receiving portion 106 of interval 42, a low first sample 110 and a high second sample 110 are together indicative of a low-to-high transition, which in turn is indicative of an encoded 0, as described above with reference to version 30 of encoding scheme 34 shown in FIG. 1. Similarly, during power-and-data-receiving portion 106 of interval 44, samples 110 are indicative of an encoded 1. Typically, the interval 112 between adjacent samples 108 or 110 is fixed at a single value, and signal 40 is continually sampled; thus, if the number of samples 108 of power signal 38 is equal to the number of samples 110 of power-and-data signal 48, intervals 104 and 106 are typically equal in length, as shown in FIG. 12.

Reference is now made to FIG. 13, which is a schematic illustration of method 37 for receiving power and data during a plurality 20 of consecutive time intervals 20, in accordance with some applications of the present invention. In some applications, during each of intervals 20, (a) receiving power-and-data signal 48 comprises sampling power-and-data signal 48 exactly 2N times, and (b) receiving power signal 38 comprises sampling power signal 38 exactly N times. For example, FIG. 13 shows signal 38 sampled once, and signal 48 sampled twice, i.e., N=1. Samples 110 are used as described above with respect to FIG. 12. Analogously to FIG. 12, FIG. 13 shows interval 106 being twice the length of interval 104, such that the number of samples 110 of power-and-data signal 48 is twice the number of samples 108 of power signal 38.

Typically, receiving power-and-data signal 48 comprises sampling power-and-data signal 48 by a receiver, e.g., receiver described above with respect to FIG. 9. Typically, the sampling is driven by an internal-clock of the receiver. For example, FIG. 13 shows an internal-clock signal 114 of receiver 77. Upon each low-to-high transition 116 of signal 114, signal 40 is sampled.

Figure 14:
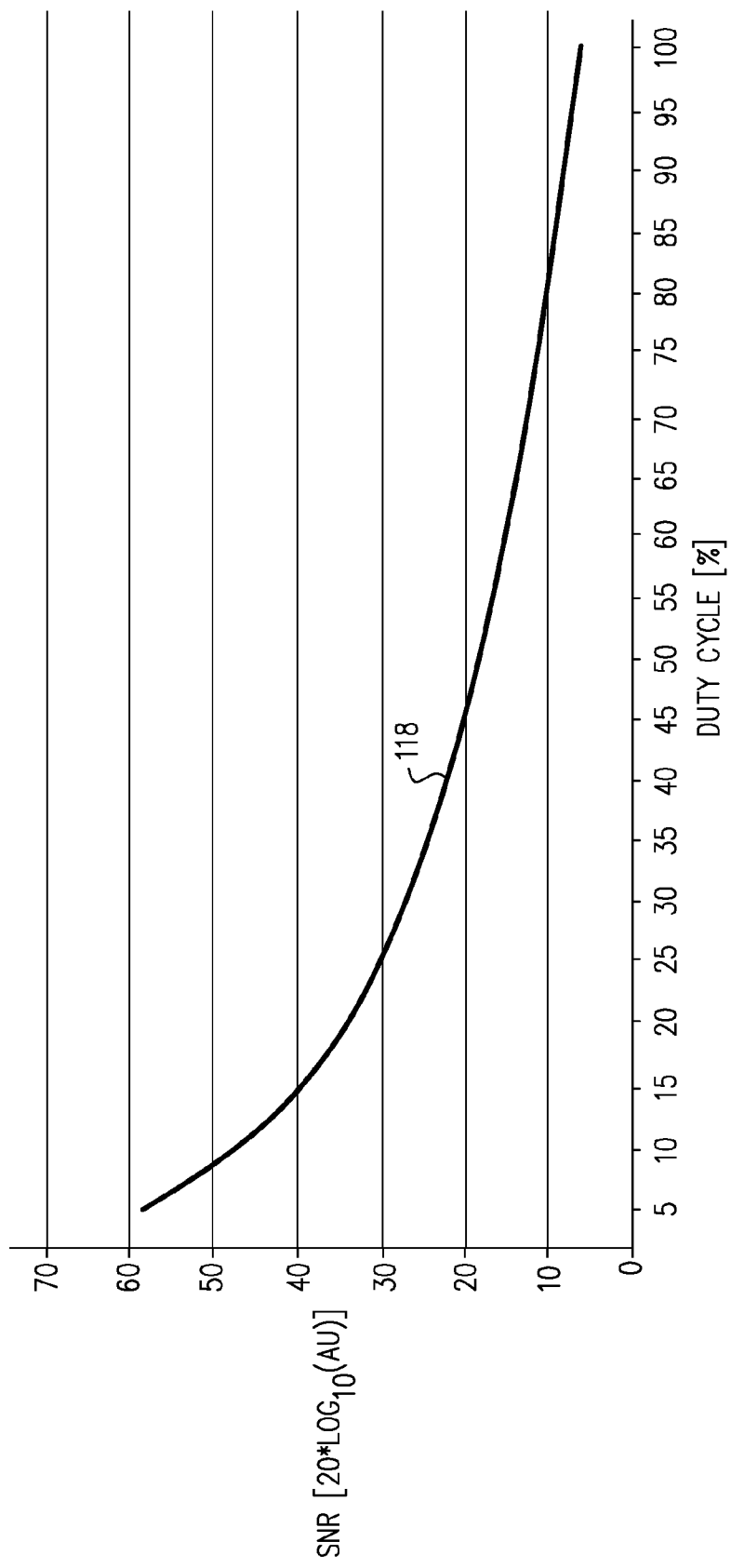
FIG. 14 shows a plot of signal-to-noise ratio (SNR) vs. duty cycle, in accordance with some applications of the present invention.
Figure 15:
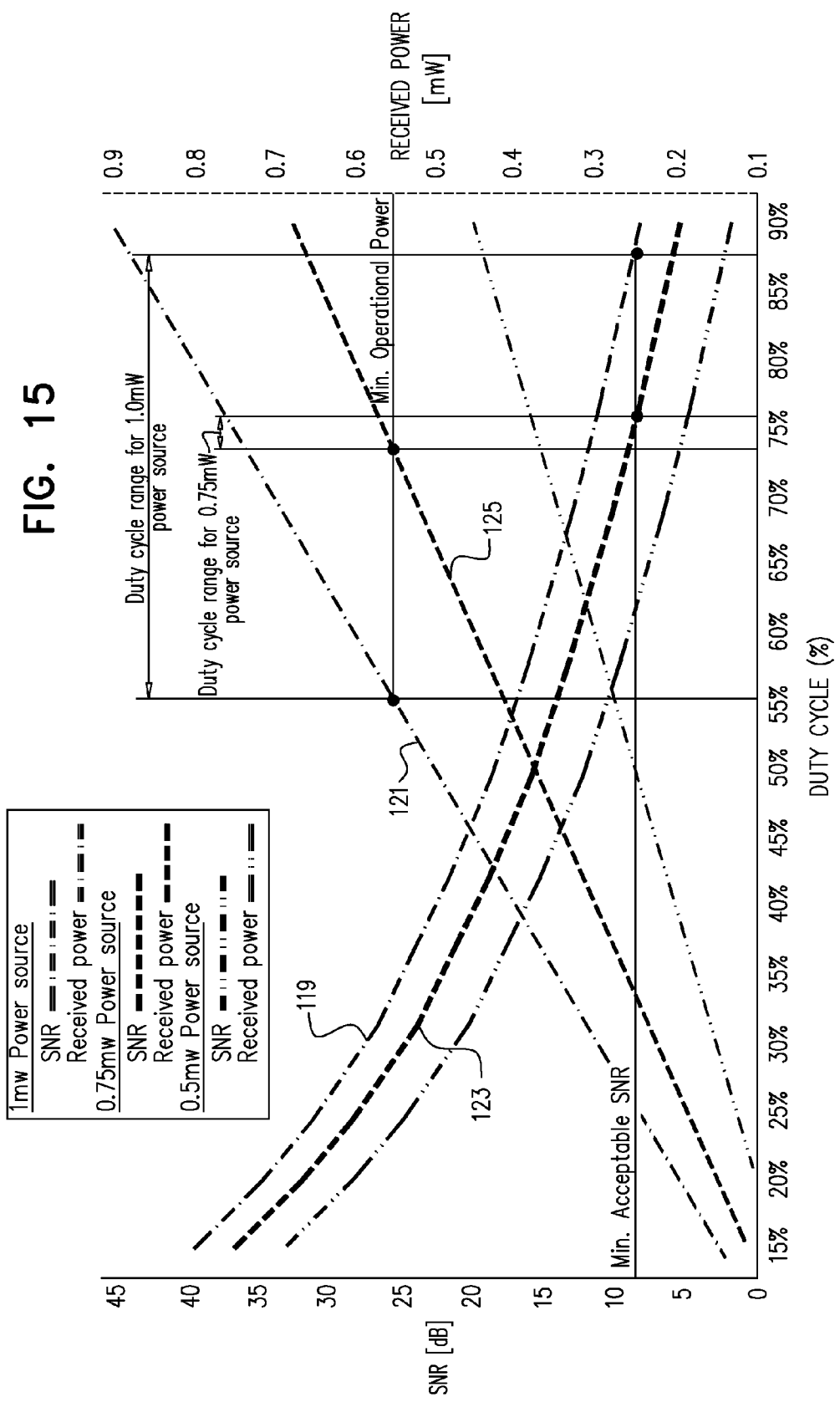
FIG. 15 shows plots of SNR and received power vs. duty cycle, in accordance with some applications of the present invention.

Reference is now made to FIG. 14, which shows a plot 118 of signal-to-noise ratio (SNR) vs. duty cycle, in accordance with some applications of the present invention. SNR is plotted on a logarithmic scale, in arbitrary units. (The exact value for the SNR at a particular duty cycle typically depends on other factors, e.g., the respective durations of time intervals 20, in addition to the duty cycle). Generally, decreasing the duration of power-and-data signal 48 (FIGS. 4A-B) decreases the SNR. Thus, as plot 118 shows, raising the duty cycle lowers the SNR, since raising the duty cycle typically involves decreasing the duration of power-and-data signal 48. As further described below with respect to FIG. 15, plot 118 may be used to determine the highest duty cycle that can be used in a given application without unacceptably compromising the SNR. In some applications of the present invention, relatively high duty cycles (e.g., 75% or greater) can be used without unacceptably compromising the SNR, due to at least the following two factors, each of which facilitates a higher SNR:

(i) the use of on-off encoded signal 60, signal 60 being at a relatively high maximum amplitude A when on (FIGS. 4A-B); and (ii) relatively long durations of time intervals 20. Relatively long durations of time intervals 20 (and hence, relatively low bit rates) are acceptable, for example, if there is a relatively small amount of data to be transferred.

Reference is now made to FIG. 15, which shows plots of SNR and received power vs. duty cycle, in accordance with some applications of the present invention. By way of non-limiting example, the plots in FIG. 15 show modeled results of using method 33 for transfer of power and data, assuming that variables such as the respective durations of time intervals 20 are fixed at particular values. SNR is plotted on a logarithmic scale, in units of dB, while received power is plotted in units of mW.

Plot 119 shows the SNR using a 1 mW power source; as the duty cycle increases, the SNR decreases, dropping below a minimum acceptable SNR of about 8 dB at a duty cycle of 87.5%. (It is noted that use of 8 dB as a minimum acceptable SNR is by way of illustration and not limitation, and that other minimum acceptable values are suitable as well.) Plot 121 shows the received power using the 1 mW power source. Below a duty cycle of 55%, the received power does not meet the minimum threshold of 0.55 mW required for operation of the receiving device. Thus, the range of acceptable duty cycles lies between 55% and 87.5%. (Use of 0.55 mW as a minimum acceptable level of received power is by way of illustration and not limitation, and that other minimum acceptable values are suitable as well.)

Typically, as described above with respect to plot 118 of FIG. 14, the plot of SNR vs. duty cycle (or another plot conveying similar information) is used to determine the highest duty cycle that can be used in a given application without unacceptably compromising the SNR. Thus, in the case illustrated by plot 119, the chosen duty cycle will typically be close to 87.5% (e.g., a duty cycle of ⅞). Nonetheless, in the case illustrated by plot 119, in some applications, a lower duty cycle that is nevertheless higher than 55% may be desired (e.g., ⅔, ¾, ⅘, or ⅚), in light of other considerations. Analysis of plot 121 together with plot 119 facilitates the choosing of an optimal duty cycle, by showing a range of acceptable duty cycles. FIG. 15 also shows the effect of varying the power source. For example, plots 123 and 125 show that using a 0.75 mW power source instead of a 1 mW power source leads to a much smaller range of acceptable duty cycles, with a maximum duty cycle of only about 75%. Typically, therefore, a duty cycle of ¾ would be selected based on the use of a received power level of 0.75 mW, in the context of the parameters underlying the model forming the basis of FIG. 15.

It is emphasized that FIG. 15 is based on a particular model of the use of method 33, and that different plots would be obtained, providing different constraints on duty cycle, if different assumptions of system performance and system requirements were used.

Reference is again made to FIG. 5. FIG. 5 shows a method 122 for use with a source set 120 of consecutive digital data bits. A signal 40, in which are encoded no more data bits than are in source set 120, is generated. (Ignoring the ellipsis in FIG. 5, the figure shows exactly eight bits encoded in signal 40, eight being the length of source set 120.) Signal 40 is transmitted using an on-off, amplitude-modulation encoding scheme, e.g., using on-off encoded signal 60, described above with respect to FIGS. 4A-B. Signal 40 is transmitted with a duty cycle that is fixed at a value of n/(n+1), n being an integer greater than 1. Typical values of n are 2, 3, and 4. For example, FIG. 5 shows signal 40 transmitted with a duty cycle of ¾, i.e., with n=3. In some applications, n may also be 5, 6, 7, or 8.

Reference is now made to FIG. 16, which is a schematic illustration of a method 124 for transmission of power and data during a plurality 20 of consecutive time intervals, in accordance with some applications of the present invention. During power-transmission portion 36 of each of intervals 20, power signal 38, in which no data is encoded, is transmitted. During power-and-data-transmission portion 46 of each of intervals 20, power-and-data signal 49, in which is encoded a single bit 54, is transmitted. Method 124 is similar to method 33, described above with respect to FIGS. 4A-B, but differs in at least one respect. Whereas power-and-data signal 48 of method 33 includes both a high-level and a low-level portion (see FIGS. 4A-B), power-and-data signal 49 of method 124 may not include both a high-level and a low-level portion. For example, as shown in FIG. 16, power-and-data signal 49 of first time interval 42 includes a single portion with amplitude B, while power-and-data signal 49 of second time interval 44 includes a single portion with amplitude A.

Reference is made to FIG. 18, which is a schematic illustration of a method 200 for transmitting power and data to an implanted device, such as retinal prosthesis 76 (FIG. 3), during a plurality 20 of consecutive time intervals, in accordance with some applications of the present invention. During each of the plurality 20 of consecutive time intervals, a power-and-data light signal 202 is transmitted. During a first sub-interval 204 of each time interval, a first power-and-data signal portion 208 of signal 202 is transmitted, and in a second sub-interval 206 of each time interval, a second power-and-data signal portion 210 of signal 202 is transmitted. First and second signal portions 208 and 210 differ in the polarization and/or the wavelength of the transmitted light; that is, first signal portion 208 has a polarization or wavelength that has a first value, while second signal portion 210 has a polarization or wavelength that has a second value distinct from the first value. For example, first signal portion 208 might be s-polarized, while second signal portion 210 is p-polarized. Alternatively or additionally, for example, first signal portion 208 might be transmitted with a wavelength of 800 nm, or with a wavelength band of 750-850 nm, while second signal portion 210 is transmitted with a wavelength of 900 nm, or with a wavelength band of 850-950 nm. (Although, as noted above, the two values are distinct from one another, they may overlap. For example, first signal portion 208 might be transmitted with a wavelength band of 750-900 nm, while second signal portion 210 is transmitted with a wavelength band of 850-1000 nm.)

Method 200 provides for a single bit 54 of data to be encoded during each of the time intervals. For example, FIG. 18 shows a "1" encoded during first time interval 42, by first signal portion 208 having a polarization or wavelength having a value A, and second signal portion 210 having a value B. (For example, A might be p-polarization, while B is s-polarization.) During second time interval 44, a "0" is encoded, by first signal portion 208 having a polarization or wavelength having value B, and second signal portion 210 having a polarization or wavelength having value A. Power from signal 202 is used to power the implanted device (e.g., retinal prosthesis 76), while bits 54 encoded in signal 202 are used to control the implanted device.

In some applications, as shown in FIG. 18, respective durations of first signal portion 208 and second signal portion 210 are configured to be the same as each other, during each of the plurality 20 of consecutive time intervals. In some applications, as shown in FIG. 18, respective durations of first signal portion 208 are configured to be the same as each other in each of at least eight consecutive time intervals 68, and/or four consecutive time intervals 70, of the plurality of consecutive time intervals. (For simplicity, the latter four intervals of the eight consecutive time intervals 68 are not explicitly shown.) In some applications, as shown in FIG. 18, respective durations of second signal portion 210 are also configured to be the same as each other, in each of eight consecutive time intervals 68, and/or four consecutive time intervals 70.

In some applications, as described above with respect to signals 38 and 48 and with reference to FIGS. 17A-B, amplitudes of first and second signal portions 208 and 210, in each of the plurality of consecutive time intervals, are configured to be dependent on a parameter that is independent of the data. In some applications, as further described above with respect to FIG. 17B signals 38 and 48 and with reference to FIGS. 17A-B, this parameter is sensed, and the amplitudes are configured to be dependent on the sensed parameter. For example, in some applications, a level of ambient light, e.g., ambient infrared and/or visible light, is sensed, and the amplitudes are configured to be dependent on the sensed level of ambient light. Typically, the amplitudes are configured to increase in response to an increased sensed level of ambient light, such as to increase the signal-to-noise ratio (SNR).

In some applications, as shown in FIG. 18, plurality 20 of consecutive time intervals includes at least eight consecutive time intervals 68 and/or four consecutive time intervals 70, and power-and-data light signal 202 is transmitted during each of time intervals 68 and/or 70.

Typically, as described above with respect to signals 38 and 48 and with reference to FIG. 3, signal 202 is an infrared power-and-data light signal 203. Typically, as described above with respect to infrared transmitter 73 and with reference to FIGS. 8A-B, infrared signal 203 is transmitted from a light-emitting diode 80 and/or a laser 82.

It is noted that an advantage of method 200 is that the method provides for a duty cycle of 100%, or close thereto, since data can be encoded in signal 202 without the signal having "off" or "low amplitude" phases. It is further noted that the scope of the present invention allows for other methods of transferring power and data that share this advantage, including methods in which at least some of time intervals 20 are not divided into first and second sub-intervals. For example, some methods may employ an encoding scheme whereby a "0" is encoded by the transmitted light having a wavelength or polarization having a first value, during the entire time interval, while a "1" is encoded by the transmitted light having a wavelength or polarization having a second value distinct from the first value, during the entire time interval.

Figure 19:
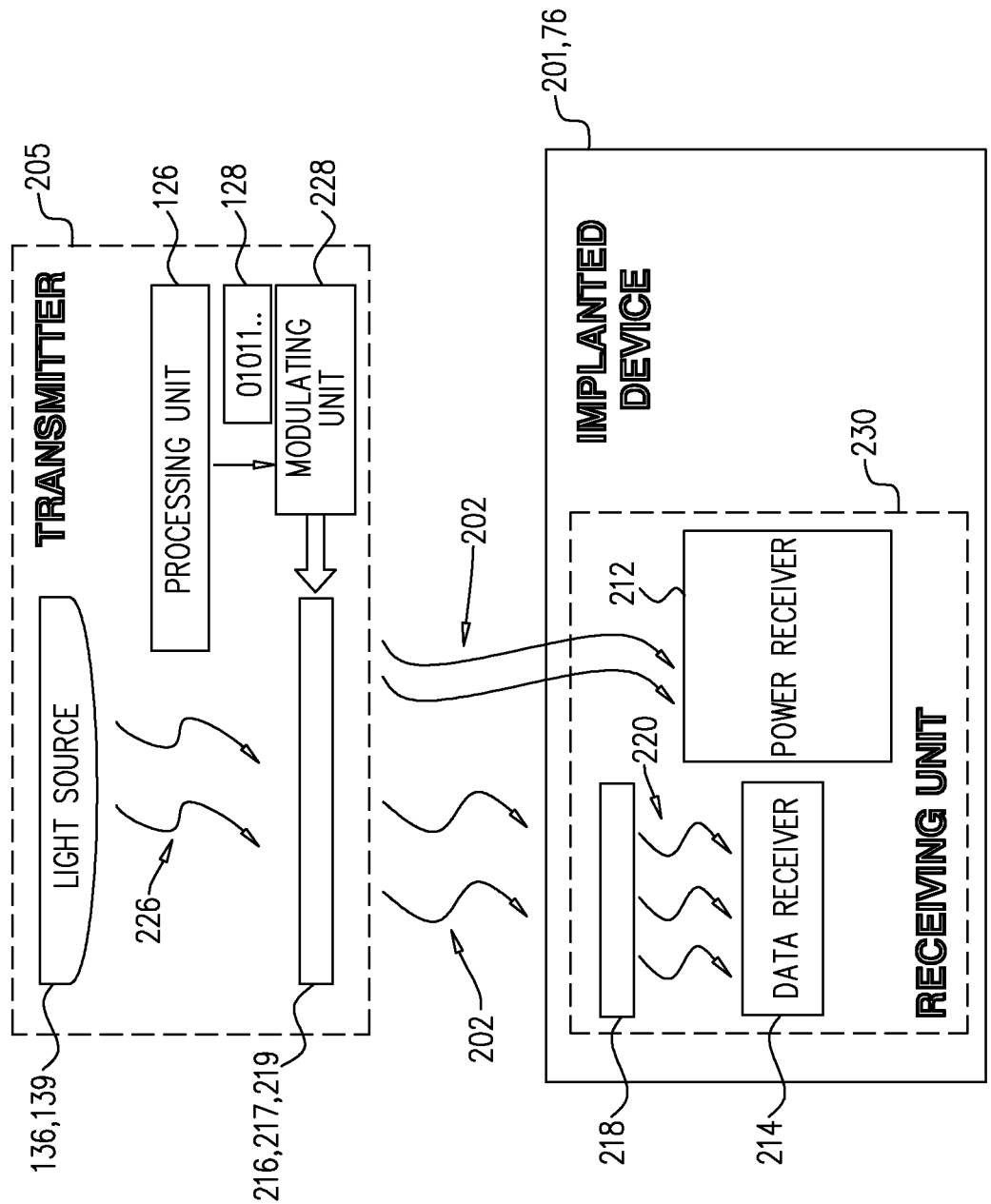
FIG. 19 is a schematic illustration of apparatus for transferring and receiving power and data, in accordance with some applications of the present invention.

Reference is now made to FIG. 19, which is a schematic illustration of apparatus for transferring and receiving power and data, in accordance with some applications of the present invention. An implanted device 201 (e.g., retinal prosthesis 76) is shown including a receiving unit 230, comprising a power receiver 212 (e.g., a photovoltaic cell), a data receiver 214 (e.g., a photodiode) that is structurally distinct from power receiver 212, and a filter 218. During each of time intervals 20, filter 218 allows passage to data receiver 214 of exactly one of (a) first signal portion 208, and (b) second signal portion 210. Thus, signal 202 is filtered to yield a data signal 220, which is received by data receiver 214. Implanted device 201 is controlled in response to data signal 220. In parallel to data receiver 214 receiving data signal 220, power receiver 212 receives signal 202, and power from signal 202 is used to power implanted device 201.

In some applications, the first and second signal portions differ with respect to their respective polarizations. For example, with reference to FIG. 18, value A might be s-polarization, while value B is p-polarization. In such applications, filter 218 is a polarizer, configured to allow passage therethrough, for example, of p-polarized light, but to block passage therethrough of s-polarized light. In some applications, the first and second signal portions differ with respect to their respective wavelengths. For example, with reference to FIG. 18, value A might be 800 nm, while value B is 900 nm. In such applications, filter 218 is a wavelength filter, configured to allow passage therethrough, for example, of wavelengths that are less than 850 nm, but to block passage therethrough of wavelengths that are greater than 850 nm.

Reference is now made to FIG. 20, which is a schematic illustration of data signal 220 as produced by the filtering action of filter 218, in accordance with some applications of the present invention. (It is noted that FIG. 20 shows the amplitude of the signal along the vertical axis, while FIG. 18 shows the value of polarization or wavelength along the vertical axis.) Data signal 220, as shown in FIG. 20, is a filtered version of signal 202 as shown in FIG. 18, assuming that filter 218 allows the passage therethrough of light having value A, but not of light having value B. During each of the time intervals, data signal 220 includes (a) a low-level data signal portion 224, corresponding to the portion of signal 202 that is blocked by filter 218, and (b) a data-signal portion 222 having an amplitude that is higher than that of low-level portion 224, data-signal portion 222 being the portion of signal 202 that passes through filter 218.

In some applications, data receiver 214 (FIG. 19) is synchronized to transmitter 205 (FIG. 19) of signal 202, in a manner generally described above with reference to FIG. 10. That is, a transition is detected during each of the time intervals, the transition being (a) between data signal portion 222 and data signal portion 224, or (b) between data signal portion 224 and data signal portion 222. By verifying that a sequence of the transitions corresponds to a synchronization sequence 86 of bits (FIG. 10), data receiver 214 is synchronized to transmitter 205. In some applications, as generally described above with reference to FIG. 10, signal 202 includes a synchronization signal 84 during at least some of time intervals 20, a bit from synchronization sequence 86 being encoded in synchronization signal 84 during each of these time intervals. In some applications, as described above with reference to FIG. 10, synchronization signal 84 is transmitted during at least sixteen consecutive time intervals.

Reference is again made to FIG. 19, which shows apparatus for transmission of power and data during a plurality of consecutive time intervals, the apparatus comprising a transmitter 205 configured to transmit signal 202. Transmitter 205 comprises (a) a processing unit 126, configured to output a sequence 128 of bits, (b) at least one light source 136, configured to emit a light beam 226, and (c) a modulating unit 228. Light source 136 typically comprises at least one infrared light source 139, and light beam 226 typically includes an infrared light beam. Modulating unit 228 is configured to, during each of plurality 20 of consecutive time intervals, encode in light beam 226 a single bit of bit sequence 128. Modulating unit 228 encodes the bit by causing the polarization or wavelength of light beam 226 to vary between first and second sub-intervals 204 and 206, thus generating signal 202, as described above with reference to FIG. 18.

In some applications, transmitter 205 further comprises an adjustable filter 216. In such applications, modulating unit 228 is configured to encode the single bit by driving adjustable filter 216 to block passage therethrough of a portion of light beam 226. During first sub-interval 204, modulating unit 228 drives filter 216 to block passage therethrough of light having the second polarization or wavelength value, while allowing passage therethrough of light having the first value. During second sub-interval 206, modulating unit 228 drives filter 216 to block passage therethrough of light having the first polarization or wavelength value, while allowing passage therethrough of light having the second value. In some applications, adjustable filter 216 comprises an adjustable polarizer 217, and modulating unit 228 drives polarizer 217 to (a) during first sub-interval 204, block light that has the second polarization, and (b) during second sub-interval 206, block light that has the first polarization. For example, if light beam 226 includes both s-polarized and p-polarized light, polarizer 217 may block the s-polarized portion of light beam 226 (but not the p-polarized portion) during first sub-interval 204, and the p-polarized portion of light beam 226 (but not the s-polarized portion) during second sub-interval 206. In other applications, adjustable filter 216 comprises an adjustable wavelength filter 219, and modulating unit 228 drives filter 219 to (a) during first sub-interval 204, block light that has the second wavelength, and (b) during second sub-interval 206, block light that has the first wavelength. For example, if light beam 226 includes light with wavelengths of 750-950 nm, polarizer 217 may block the 750-850 nm portion of light beam 226 (but not the 850-950 nm portion) during first sub-interval 204, and the 850-950 nm portion of light beam 226 (but not the 750-850 nm portion) during second sub-interval 206.

Reference is now made to FIGS. 21A-B, which are schematic illustrations of apparatus for transmission of power and data during plurality 20 of consecutive time intervals, in accordance with some applications of the present invention. In some applications, modulating unit 228 is configured to encode the single bit from sequence 128, during each of time intervals 20, by driving light source 136 to emit light having a wavelength or polarization that varies between sub-intervals 204 and 206, in the manner described above with reference to FIG. 18. That is, during first sub-interval 204, light source 136 is driven to emit light having a first polarization (e.g., s-polarization) or wavelength (e.g., 750-850 nm), and during second sub-interval 206, light source 136 is driven to emit light having a second polarization (e.g., p-polarization) or wavelength (e.g., 850-950 nm). FIG. 21A shows a single light source 136, while FIG. 21B shows light source 136 comprising first and second transmitting elements (e.g., first and second light sources) 137a and 137b. In the application shown in FIG. 21B, first light source 137a emits light having the first polarization or wavelength, while light source 137b emits light having the second polarization or wavelength. During the transmission of signal 202, no more than one of light sources 137a and 137b is transmitting at any given time. In other words, neither one of light sources 137a and 137b emits signal 202 on its own, but rather, the two light sources together emit signal 202.

An advantage of having two light sources, as shown in FIG. 21B, is that transmitter 205 can be configured to transmit a power-only light signal that provides approximately twice as much power to the implanted device, relative to the application shown in FIG. 21A. This is accomplished by having a power-only signal period, during which light beam 226 includes light emitted simultaneously from both light sources, and modulating unit 228 does not encode any data in the light beam.

In some applications, transmitter 205 as shown in FIGS. 19 and 21A-B further comprises memory array 130, as described above with reference to FIG. 9. In some applications, the transmitting apparatus as shown in FIGS. 19 and 21A-B is for use with user interface 140, as described above with reference to FIG. 9. In some applications, transmitter 205 as shown in FIGS. 19 and 21A-B is configured to be mounted on eyeglasses 74 of subject 78 and to transmit signal 202 toward retinal prosthesis 76, as described above with reference to FIG. 3. Typically, as described above with respect to infrared transmitter 73 and with reference to FIGS. 8A-B, infrared light source 139 comprises a light-emitting diode 80 and/or a laser 82.

Referring to FIGS. 19 and 21A-B, in some applications, modulating unit 228 is configured to modulate filter 216 or light source 136 such as to make signal 202 have one or more of the properties described above with reference to FIG. 18. For example, in some applications, modulating unit 228 is configured to make respective durations of (a) first sub-interval 204, and (b) second sub-interval 206, the same as each other, during each of the plurality 20 of consecutive time intervals.

It is noted that the scope of the present invention allows for the invention to be applied to any type of data that can be represented digitally. For example, applications of the invention can be used to transfer power and image data to a receiving device. Furthermore, although portions of the description above relate to a retinal prosthesis, the scope of the present invention allows for any type of power-and-data-receiving device to receive the power-and-data signal.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for transmission of power and data during a plurality of consecutive time intervals, the method comprising:
during a power-transmission portion of each of the plurality of consecutive time intervals, transmitting a power signal in which no data is encoded;
during a power-and-data-transmission portion of each of the plurality of consecutive time intervals, transmitting a power-and-data signal in which is encoded a single bit, the power-and-data signal including: (a) a high-level power-and-data signal portion, and (b) a low-level power-and-data signal portion, the high-level power-and-data signal portion being higher than the low-level power-and-data signal portion; and
configuring a transmission duty cycle in each of the plurality of consecutive time intervals to be n/(n+1), n being an integer greater than one.

2. The method according to claim 1, further comprising configuring (i) a maximum amplitude of the power signal, and (ii) a maximum amplitude of the power-and-data signal, in each of the plurality of consecutive time intervals, to be independent of the data.

3. The method according to claim 1, wherein:
the power-and-data signal includes a synchronization signal, in which is encoded a bit from a synchronization sequence of bits, during at least some of the plurality of consecutive time intervals, and
transmitting the power-and-data signal comprises transmitting the synchronization signal.

4. A method for receiving power and data during a plurality of consecutive time intervals, the method comprising:
during a power-receiving portion of each of the plurality of consecutive time intervals, receiving a power signal in which no data is encoded;
during a power-and-data-receiving portion of each of the plurality of consecutive time intervals, receiving a power-and-data signal in which is encoded a single bit, the power-and-data signal including: (a) a high-level power-and-data signal portion, and (b) a low-level power-and-data signal portion, the high-level power-and-data signal portion being higher than the low-level power-and-data signal portion; and
wherein receiving the power-and-data signal comprises receiving the power-and-data signal by a receiver, and wherein the method further comprises synchronizing the receiver to a transmitter of the power-and-data signal by:
detecting a transition during each of the time intervals, the transition selected from the group consisting of: (i) a transition between the high-level power-and-data signal portion and the low-level power-and-data signal portion, and (ii) a transition between the low-level power-and-data signal portion and the high-level power-and-data signal portion, and
verifying that a sequence of the transitions corresponds to a synchronization sequence.

5. Apparatus for transmission of power and data during a plurality of consecutive time intervals, the apparatus comprising a transmitter comprising:
a processing unit, configured to output a sequence of bits;
a modulating unit, configured to convert the sequence to an analog signal; and
a light source, configured to transmit a light signal in response to the analog signal, the light signal including:
during a power-transmission portion of each of the plurality of consecutive time intervals, a power signal in which no data is encoded, and
during a power-and-data-transmission portion of each of the plurality of consecutive time intervals, a power-and-data signal in which is encoded a single bit, the power-and-data signal including: (a) a high-level power-and-data signal portion, and (b) a low-level power-and-data signal portion, the high-level power-and-data signal portion being higher than the low-level power-and-data signal portion; and wherein the modulating unit is configured to make a transmission duty cycle, in each of the plurality of consecutive time intervals, have a value n/(n+1), n being an integer greater than one.

6. The apparatus according to claim 5, wherein:
the transmitter further comprises a memory array, configured to store the sequence of bits output by the processing unit, and
the modulating unit is configured to read the sequence from the memory array and convert the sequence to the analog signal.

7. The apparatus according to claim 5, wherein the apparatus is for use with a user interface, and wherein the processing unit is configured to output the sequence of bits in response to input from the user interface.

8. The apparatus according to claim 5, wherein the apparatus is for use with a retinal prosthesis implanted in a subject, and wherein the transmitter is configured to be mounted on eyeglasses of the subject and to transmit the power signal and the power-and-data signal toward the retinal prosthesis.

9. The apparatus according to claim 5, wherein the light source comprises an infrared light source configured to transmit an infrared light signal, the infrared light signal including the power signal and the power-and-data signal.

10. The apparatus according to claim 5, wherein the apparatus further comprises a sensor configured to sense a level of ambient light, and wherein the modulating unit is configured to regulate the transmission duty cycle in response to the sensed level of ambient light.

11. The apparatus according to claim 5, wherein the modulating unit is configured to regulate (i) a maximum amplitude of the power signal, and (ii) a maximum amplitude of the power-and-data signal, in each of the plurality of consecutive time intervals, independently of the data.

12. The apparatus according to claim 5, wherein the modulating unit is configured to make the transmission duty cycle, in each of the plurality of consecutive time intervals, have a value between 65% and 90%.

13. The apparatus according to claim 5, wherein the light signal includes an amplitude-modulated signal, and wherein the light source is configured to transmit the amplitude-modulated signal.

14. The apparatus according to claim 13, wherein the amplitude-modulated signal includes a Manchester encoded signal, and wherein the light source is configured to transmit the Manchester encoded signal.

15. The apparatus according to claim 5, wherein, for each of the plurality of consecutive time intervals, the modulating unit is configured to make a length of the power transmission portion be between 30% and 80% of a length of the time interval.

16. The apparatus according to claim 5, wherein:
the power-and-data signal includes a synchronization signal, in which is encoded a bit from a synchronization sequence of bits, during at least some of the plurality of consecutive time intervals, and
the light source is configured to transmit the synchronization signal.

* * * * *